United States Patent
Schulz et al.

(10) Patent No.: US 6,281,399 B1
(45) Date of Patent: Aug. 28, 2001

(54) PRODUCTION OF ISOPROPYL AROMATICS BY PASSING PORTIONS OF TRANSALKYLATION EFFLUENT TO A MULTI-BED ALKYLATION ZONE

(75) Inventors: Russell C. Schulz, Glen Ellyn; Gregory J. Gajda; Guy B. Woodle, both of Mount Prospect, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/511,612

(22) Filed: Feb. 23, 2000

Related U.S. Application Data

(63) Continuation-in-part of application No. 09/124,205, filed on Jul. 28, 1998, now Pat. No. 6,096,935.

(51) Int. Cl.⁷ .............................. C07C 2/66; C07C 2/68; C07C 5/52
(52) U.S. Cl. ................ 585/323; 585/449; 585/467; 585/475
(58) Field of Search ................ 585/323, 449, 585/467, 475

(56) References Cited

U.S. PATENT DOCUMENTS

| | | | |
|---|---|---|---|
| 4,008,290 | 2/1977 | Ward | 260/672 T |
| 4,051,191 | 9/1977 | Ward | 260/671 R |
| 4,083,886 | 4/1978 | Michalko | 260/672 T |
| 4,587,370 | 5/1986 | DeGraff | 585/450 |
| 4,695,665 | 9/1987 | DeGraff | 585/450 |
| 4,891,458 | 1/1990 | Innes et al. | 585/323 |
| 4,922,053 | 5/1990 | Waguespack et al. | 585/449 |
| 5,003,119 | 3/1991 | Sardina et al. | 585/323 |
| 5,030,786 | 7/1991 | Shamshoum et al. | 585/467 |
| 5,177,285 | 1/1993 | Van Opdorp et al. | 585/467 |
| 5,336,821 | 8/1994 | DeGraff et al. | 585/402 |
| 5,723,710 | 3/1998 | Gajda et al. | 585/467 |
| 5,902,917 | 5/1999 | Collins et al. | 585/323 |
| 5,998,684 | 12/1999 | Ho et al. | 585/323 |
| 6,096,935 | * 8/2000 | Schutz et al. | 585/323 |

FOREIGN PATENT DOCUMENTS 733 608 A1    9/1996  (EP) .

* cited by examiner

Primary Examiner—Walter D. Griffin
Assistant Examiner—Thuan D. Dang
(74) Attorney, Agent, or Firm—John G. Tolomei; John F. Spears, Jr.; Michael A. Moore

(57) ABSTRACT

A process for producing isopropyl aromatics using a transalkylation reaction zone and an alkylation reaction zone is disclosed. Portions of the transalkylation reaction zone effluent pass to a multibed alkylation reaction zone where aromatics in the transalkylation reaction zone effluent are alkylated to the desired isopropyl aromatics. At least a portion of the transalkylation reaction zone effluent passes to an alkylation bed other than the first alkylation bed of the multibed alkylation reaction zone. This process decreases the capital and operating costs of recycling the aromatics in the transalkylation reaction zone effluent. This process is well suited for solid transalkylation and alkylation catalysts. Cumene may be produced by this process.

33 Claims, 3 Drawing Sheets

PRODUCTION OF ISOPROPYL AROMATICS BY PASSING PORTIONS OF TRANSALKYLATION EFFLUENT TO A MULTI-BED ALKYLATION ZONE

ROSS-REFERENCE TO RELATED APPLICATION

This application is a continuation-in-part application of U.S. patent application Ser. No. 09/124,205, filed Jul. 28, 1998 now U.S. Pat. No. 6,096,935.

FIELD OF THE INVENTION

This invention relates to a hydrocarbon conversion process. The invention more specifically relates to the production of alkylaromatic hydrocarbons by the reaction of an acyclic olefinic hydrocarbon with an aromatic feed hydrocarbon.

BACKGROUND OF THE INVENTION

The alkylation of aromatics with olefins to produce monoalkyl aromatics is a well developed art which is practiced commercially in large industrial units. One commercial application of this process is the alkylation of benzene with ethylene to produce ethylbenzene which is subsequently used to produce styrene. Another application is the alkylation of benzene with propylene to form cumene (isopropylbenzene) which is subsequently used in the production of phenol and acetone. Those skilled in the art are therefore familiar with the general design and operation of such alkylation processes.

The performances of alkylation processes for producing monoalkyl aromatics are influenced by the stability and activity of the solid catalyst at the operating conditions of the process. For example, as the molar ratio of aromatic per olefin increases, currently available catalysts typically exhibit an improved selectivity to the monoalkyl aromatic. But even at a high molar ratio of aromatic per olefin, several polyalkyl aromatic by-products such as dialkyl aromatics and trialkyl aromatics accompany monoalkyl aromatic production.

Although the formation of dialkyl and trialkyl aromatics might, at first glance, be viewed as by-products that represent a reduction in the efficient use of the olefin, in fact each can be readily transalkylated with the aromatic using a transalkylation catalyst to produce the monoalkyl aromatic. So-called combination processes combine an alkylation zone with a transalkylation zone in order to maximize monoalkyl aromatic production.

One disadvantage of combination processes is that separate reaction zones for alkylation and for transalkylation duplicate costly equipment. Each reaction zone requires what amounts to its own reaction train, including separate and independent reaction vessels, heaters, heat exchangers, piping, and instrumentation.

Another disadvantage of combination processes is the great expense associated with recovering and recycling unreacted aromatic from the effluents of the alkylation and transalkylation reaction zones. Alkylation reaction zones generally operate at a molar ratio of aromatic per alkylation agent that is at least 1:1 in order to ensure a high selectivity toward the monoalkyl aromatic. Transalkylation reaction zones generally operate at a molar ratio of aromatic per dialkyl aromatic that is much greater than the stoichiometric ratio of 1:1 in order to ensure a high conversion of the dialkyl aromatic to the monoalkyl aromatic. Consequently, the alkylation and transalkylation reaction zone effluents contain a significant quantity of unreacted aromatic, which must be removed in order to obtain the monoalkyl aromatic product and which must be recycled in order to ensure the efficient use of the aromatic.

Prior art combination processes lessen the great expense incurred in removing and recycling the unreacted aromatic contained in the alkylation and transalkylation reaction zone effluents by routing each alkylation and transalkylation effluent stream to a single, common product recovery facility, in which the very same distillation columns remove unreacted aromatic from both effluent streams and recycle unreacted aromatic to both reaction zones. Incidentally, a no less important function of these distillation columns in the prior art is the removal of polyalkyl aromatics other than dialkyl and trialkyl aromatics and of other heavy alkylation and transalkylation by-products such as diphenylalkanes, which are collectively referred to herein as heavies. Although sharing common product equipment in this manner reduces the capital expense of a combination process, the energy requirements for vaporizing and condensing the aromatic from the effluent streams remains undiminished.

Thus, the high utilities expenses of combination processes as well as the costly duplication of reaction zones has given impetus to research with a goal of minimizing energy requirements and of integrating the alkylation and transalkylation zones even further.

SUMMARY OF THE INVENTION

This invention is an economical and efficient combination process for producing an isopropyl aromatic by alkylation and by transalkylation. In this invention, portions of the transalkylation effluent stream pass to two or more alkylation beds of a multibed alkylation reaction zone. In one broad embodiment, this invention places the transalkylation and alkylation reaction zones in series, with polyisopropyl aromatics passing to the transalkylation reaction zone with the aromatic alkylation substrate, which is usually benzene, and with portions of the transalkylation effluent passing to two or more beds in a series flow arrangement in the multibed alkylation reaction zone. The alkylation beds to which portions of the transalkylation effluent pass may, but need not be, consecutive beds in the series of beds, and may or may not include the first bed of the series. This invention decreases the formation of polyisopropyl aromatics, especially diisopropyl aromatics, in the alkylation reaction zone, because polyisopropyl aromatics that are present in the transalkylation effluent and which this invention passes to the alkylation zone tend to inhibit the production of polyisopropyl aromatics in the alkylation reaction zone. Because the alkylation reaction zone makes less polyisopropyl aromatics, the transalkylation reaction zone does not need to convert as many polyisopropyl aromatics, and, therefore, the capital and operating costs associated with recycling the alkylation substrate to the transalkylation reaction zone in a combination alkylation-transalkylation process decrease.

Since some alkylation beds in this invention process only a portion of the flow from the transalkylation effluent, those alkylation beds operate at a decreased space velocity in comparison to alkylation beds in the prior art that process the entire flow from the transalkylation effluent. Alkylation beds that do, not receive the entire flow from the transalkylation reaction zone have a total flow rate that is lower than those alkylation beds that do receive the entire flow. Advantage can be taken of this reduction in space velocity to reduce the amount of catalyst in those beds and/or to adjust the flow of alkylating agent to those beds.

The benefits associated with passing portions of the transalkylation effluent to beds other than the first bed in the series of beds of the alkylation zone can be further increased by introducing the alkylation substrate into beds of the alkylation zone. It is now believed that adding additional quantities of alkylation substrate to the alkylation beds, while passing portions of the transalkylation effluent to alkylation beds other than the first of a series of alkylation beds, can decrease the net formation of heavies such as diphenylpropane and alkylated diphenylpropanes. Significantly, it is believed also that there is a synergistic decrease in the formation of these heavies when particular distributions of transalkylation effluent portions to the alkylation beds are used in cooperation with particular distributions of alkylation substrate portions to the alkylation beds. In particular, fewer heavies tend to form when, in an arrangement of alkylation beds in series, the transalkylation effluent portion(s) directed to the upstream alkylation bed(s) are generally smaller than the transalkylation effluent portion(s) directed to the downstream bed(s) while the alkylation substrate portion(s) directed to the upstream alkylation bed(s) are generally larger than the alkylation substrate portion(s) directed to the downstream bed(s). The benefit of decreased heavies formation can, in some circumstances, outweigh the costs associated with recycling the alkylation substrate that are incurred when alkylation substrate that could be diverted to the transalkylation reaction zone is instead introduced directly to the alkylation reaction zone.

The costs associated with recycling the alkylation substrate can be decreased by diverting to the transalkylation reaction zone some or all of the alkylation substrate that passes directly to the alkylation reaction zone in some prior art processes. Because diverting this benzene to the transalkylation reaction zone increases conversion of polyalkyl aromatics in the transalkylation reaction zone, the alkylation reaction zone may be operated with less alkylation substrate being passed directly to the alkylation reaction zone. Thus, less excess alkylation substrate is present in the alkylation effluent stream and, therefore, less capital and utilities need to be spent to recover the desired alkylaromatic product from the excess alkylation substrate in the alkylation effluent stream. Consequently, this invention can be operated in a manner that vaporizes, condenses, and recycles a decreased quantity not only of polyalkyl aromatics but also of excess alkylation substrate. Additional cost savings are attainable with this invention by consolidating the alkylation and transalkylation reaction zones into a single reactor vessel, and by eliminating in whole or in part recycling of the alkylation effluent stream, if any, to the alkylation reaction zone. Thus, in summary, a combination process that uses this invention can operate with significantly lower capital and utility costs compared to a prior art combination process.

Combination processes that will benefit most from this invention include those in which passing the transalkylation reactor effluent to the alkylation reaction zone does not have significant adverse effects on the production of monoalkyl aromatic in the alkylation zone or on the deactivation rate of the alkylation catalyst. For this reason, this invention is particularly applicable to combination processes that use beta zeolite as the alkylation catalyst, because at alkylation conditions beta zeolite produces nearly the equilibrium amount of monoalkyl aromatic and because, surprisingly, beta zeolite is not rapidly deactivated by polyalkyl aromatics in the alkylation feed. This invention is also particularly applicable to those combination processes that benefit from operation at a relatively high molar ratio of phenyl groups per alkyl group in the transalkylation reaction zone and a relatively low molar ratio of aromatic per alkyl group in the alkylation reaction zone.

In a broad embodiment, this invention is a process for producing isopropyl aromatic hydrocarbons. A first transalkylation feed stream comprising an aromatic substrate hydrocarbon passes to a transalkylation reaction zone. A second transalkylation feed stream comprising a first isopropyl aromatic hydrocarbon having more than one isopropyl group passes also to the transalkylation reaction zone. In the transalkylation reaction zone, the aromatic substrate hydrocarbon transalkylates with the first isopropyl aromatic hydrocarbon in the presence of a first solid catalyst to produce a second isopropyl aromatic hydrocarbon having at least one more isopropyl group than the aromatic substrate hydrocarbon. A transalkylation effluent stream comprising the aromatic substrate hydrocarbon and the second isopropyl aromatic hydrocarbon is recovered from the transalkylation reaction zone. A first alkylation feed stream comprising propylene passes to a first bed of an alkylation reaction zone. A first aliquot portion of the transalkylation effluent stream passes also to the first bed of the alkylation reaction zone. In the first bed, propylene alkylates the aromatic substrate hydrocarbon in the presence of a second solid is catalyst to produce a first bed effluent stream comprising the second isopropyl aromatic hydrocarbon. At least a portion of the first bed effluent stream and a second aliquot portion of the transalkylation effluent stream pass to a second bed of the alkylation reaction zone. In the second bed, propylene alkylates the aromatic substrate hydrocarbon in the presence of a third solid catalyst to produce the second isopropyl aromatic hydrocarbon. The second isopropyl aromatic hydrocarbon is recovered from the process.

INFORMATION DISCLOSURE

Prior art alkylation processes are well described in the literature.

U.S. Pat. No. 4,051,191 describes catalysts, reaction conditions, and a separation method for the recovery of cumene that uses a rectification zone and a two-column fractionation train.

U.S. Pat. Nos. 4,695,665 and 4,587,370 are particularly directed to the separation of products and the recovery of recycle streams from processes for the alkylation of aromatic hydrocarbons, and U.S. Pat. No. 4,695,665 discloses the use of a flash drum in combination with an effluent rectifier to recover unreacted feed components.

U.S. Pat. No. 4,891,458 describes the use of beta zeolite for the alkylation of aromatic hydrocarbons with alkenes to produce alkyl aromatics. U. S. Pat. No. 4,891,458 also discloses that transalkylation can occur in an alkylation reactor, and that additional monoalkyl aromatic hydrocarbons can be produced in an alkylation reactor by recycling polyalkyl aromatic hydrocarbons to the alkylation reactor to undergo transalkylation.

U.S. Pat. No. 4,922,053 describes a process for alkylating benzene with ethylene in a multibed reactor wherein polyethylbenzenes are recycled to the first alkylation bed and also to one or more of the other alkylation beds in order to increase ethylbenzene yield.

U.S. Pat. No. 5,030,786 discloses an alkylation process wherein the feed stream is dehydrated to enhance the performance of beta or Y zeolites in the alkylation process.

U.S. Pat. No. 5,336,821 describes the use of beta zeolite for the alkylation of aromatic hydrocarbons in a process that is improved by an indirect heat exchanger to recover the heat of reaction. In one embodiment, the alkylation reactor effluent passes through the heat exchanger and is recycled to the alkylation reactor.

Prior art transalkylation processes are well described in the literature. U.S. Pat. No. 4,083,886 describes a process for the transalkylation of the alkyl aromatic hydrocarbons that uses a zeolitic catalyst. U.S. Pat. No. 4,891,458 describes the use of beta zeolite for the transalkylation of aromatic hydrocarbons with polyalkyl aromatic hydrocarbons. European Patent Application EP 0 733 608 A1 discloses the use of an alumina silicate catalyst having an average crystal size of less than about 0.5 microns for the transalkylation of polyalkyl benzenes with benzene in a reaction zone with an alkylating agent such as ethylene.

Combination processes that produce alkyl aromatic products by using an alkylation reaction zone and a transalkylation reaction zone are also well known.

U.S. Pat. No. 4,008,290 describes a combination process in which the alkylation effluent and the transalkylation effluent are passed to a common separation zone, which separates the two effluents into product, by-product, and recycle streams including a recycle benzene stream. A portion of the alkylation effluent is recycled to the alkylation reaction zone in order to decrease the portion of the recycle benzene stream that is recycled to the alkylation reaction zone.

U.S. Pat. No. 5,003,119 describes a combination process for producing monoalkyl aromatics in which the alkylation effluent passes to the transalkylation reaction zone, and the transalkylation effluent passes to a separation zone. U.S. Pat. No. 5,003,119 also describes passing dialkyl aromatics to the alkylation reaction zone.

U.S. Pat. No. 5,177,285 discloses an alkylation process that is improved by maintaining the feed to the alkylation zone in a relatively wet condition and the feed to the transalkylation zone in a relatively dry condition. The process operates with a relatively pure ethylene feed as an alkylating agent with a large excess of benzene.

U.S. Pat. No. 5,723,710 describes a surface-modified zeolite beta which exhibits stability and long catalyst life when used in alkylation and transalkylation of aromatic compounds. The teachings of U.S. Pat. No. 5,723,710 are incorporated herein by reference.

U.S. Pat. No. 5,902,917 describes a process for producing alkylaromatics, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene.

U.S. Pat. No. 5,998,684 describes a process for producing alkylaromatics that operates with an alkylation zone and a transalkylation zone, where the transalkylation zone and the alkylation zone are arranged for series flow and the transalkylation zone effluent is passed with an aromatic containing feed and the olefinic feed, which is preferably propylene or ethylene, to the alkylation zone.

DETAILED DESCRIPTION OF THE INVENTION

Figure 1:
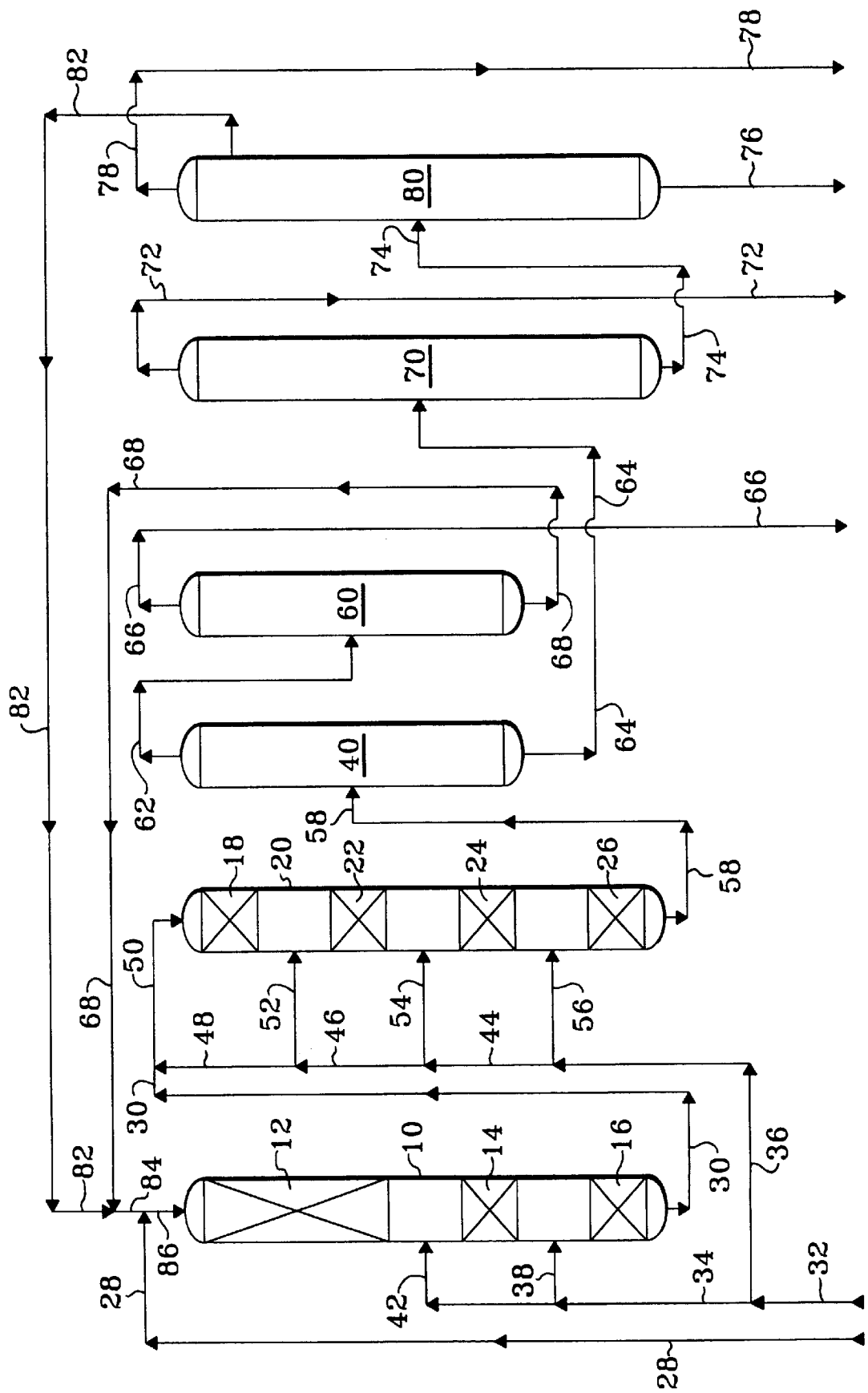
FIGS. 1, 2, and 3 are schematic illustrations of embodiments of the invention.

This invention is suitable generally for alkylation substrates and alkylation agents, and more specifically to aromatic alkylation substrates and olefinic alkylating agents. Benzene is the aromatic alkylation substrate of principal interest, but alkyl-substituted benzenes may be used. More than one aromatic alkylation substrate may be used. Monoolefins are the principal olefinic alkylating agent, but other diolefins, polyolefins, acetylenic hydrocarbons, and substituted hydrocarbons can be used. The olefinic alkylating agent preferably contains 3 carbon atoms, but olefins having from 2 to 20 carbon atoms may be used. Propylene is the preferred olefinic alkylating agent. More than one olefin may be used.

In addition to alkylation substrates and alkylation agents, this invention may also be suitable for transalkylation agents. The transalkylation agent transalkylates with the alkylation substrate to produce the desired product, namely the product of alkylating the alkylation substrate with the alkylating agent. The transalkylation agent may be introduced to the present invention via a feed from a source that is external to the present invention, but more commonly the transalkylation agent is a by-product of alkylating the alkylation substrate with the alkylating agent in the process that uses the present invention. Where the transalkylation agent is such an alkylation by-product, a transalkylation agent from an external source may not be needed, and the transalkylation agent can be passed to the transalkylation zone by recovering the transalkylation agent from the alkylation effluent stream and passing a stream enriched in transalkylation agent and depleted in desired product to the transalkylation reaction zone. Alternately and less preferably, some of the alkylation effluent stream may be passed without separation to the transalkylation reaction zone. This invention is suitable specifically for aromatic transalkylation agents having more than one isopropyl group, and diisopropyl benzenes are the principal aromatic transalkylation agents for producing monoisopropyl benzenes. As the number of alkyl groups on the desired aromatic product increases, the number of alkyl groups on the principal aromatic transalkylation agent increases.

Generally, the alkylation substrate, alkylation agent, and transalkylation agent are hydrocarbons. As used herein, the term "hydrocarbon" means a compound that contains carbon and hydrogen and that may contain other atoms as well, such as halogens (e.g., fluorine, chlorine, and bromine), oxygen, sulfur, and nitrogen. These other atoms may be present, for example, in substituent groups that are substituted on the aromatic ring of an aromatic alkylation substrate or of an aromatic transalkylation agent.

The desired alkyl aromatic product has at least one more alkyl group than the aromatic substrate. One of the widely practiced hydrocarbon conversion processes to which this invention is applicable is the production of cumene by alkylation of benzene with propylene and by transalkylation of benzene with polyisopropylbenzenes that are alkylation by-products. Therefore, the discussion herein of this invention refers mainly to cumene processes. For the sake of clarity, the discussion herein of cumene transalkylation precedes that of cumene alkylation because an essential element of this invention is passing some transalkylation effluent to the alkylation zone. It is not intended that this discussion limit the scope of this invention as set forth in the claims.

In the transalkylation reaction zone, diisopropylbenzene and higher polyisopropylbenzenes transalkylate with benzene to produce cumene (isopropylbenzene). Generally, a catalyst promotes the transalkylation in the transalkylation reaction zone. The transalkylation catalyst for the present invention may be one of a class of aluminosilicate molecular sieves known as zeolites. The zeolitic molecular sieves suitable for use in the present invention are crystalline aluminosilicates which in the calcined form may be represented by the general formula:

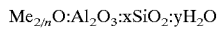

$$Me_{2/n}O:Al_2O_3:xSiO_2:yH_2O$$

where Me is a cation, n is the valence of the cation, x has a value of from about 5 to 100, and y has a value of from about 2 to 10. Detailed descriptions of zeolites may be found in D. W. Breck, *Zeolite Molecular Sieves*, John Wiley and Sons, New York 1974, and in other standard references. Suitable zeolites for the transalkylation catalyst include zeolite Y, zeolite beta, ZSM-5, PSH-3, MCM-22, MCM-36, MCM49, and MCM-56. In general, each of the zeolites described hereinafter as suitable for the alkylation catalyst is suitable for the transalkylation catalyst. A preferred zeolite Y for transalkylation is essentially free of residual non-H$^+$ cations, by which it is meant that the non-H$^+$ cation content of the zeolite Y is less than 200 wppm calculated as NH$_3$ equivalents. A preferred zeolite for the transalkylation catalyst is zeolite beta as disclosed in U.S. Pat. Nos. 4,891,458 and 5,081,323, the teachings of which are incorporated herein by reference. Another preferred zeolite beta is the surface-modified zeolite beta that is described hereinafter and which is disclosed in U.S. Pat. No. 5,723,710, the teachings of which are incorporated herein by reference. The zeolite is generally present in an amount of at least 50 wt-% of the catalyst and more preferably in an amount of at least 90 wt-% of the catalyst. In most cases, the balance of the transalkylation catalyst other than the zeolite is a refractory inorganic oxide binder. The preferred inorganic oxide is alumina, with gamma-alumina, eta-alumina, and mixtures thereof being particularly preferred. Where the catalyst comprises a zeolite and an inorganic oxide, the zeolite content may be from 5 to 99 wt-% of the catalyst, and the inorganic oxide may be from 1 to 95 wt-% of the catalyst. Preferred transalkylation catalysts are zeolite Y with an alumina or silica binder and zeolite beta with an alumina or silica binder.

The transalkylation reaction can be carried out in a broad range of operating conditions that result in a high conversion of diisopropylbenzene (DIPB) to cumene. DIPB conversion is limited by equilibrium governed mainly by the ratio of phenyl groups per alkyl group and is generally greater than 30% and preferably greater than 50%. Operating conditions generally include a temperature of from about 210° F. (99° C.) to about the critical temperature of the alkylation substrate, which is about 554° F. (290° C.) for benzene and may be 889° F. (475° C.) or even higher for heavier alkylation substrates. The transalkylation pressure would generally be from 1 to about 130 atmospheres, but set so that the reactants are in the liquid phase. Accordingly, the preferred pressure for the transalkylation reaction zone range is from 10 to about 50 atmospheres. A total liquid hourly space velocity (LHSV) of from 0.5 to 50 hr$^{-1}$ is desirable, with 0.5 to 5 hr$^{-1}$ being preferred. As used herein, the abbreviation 'LHSV" means liquid hourly space velocity, which is defined as the volumetric flow rate of liquid per hour divided by the catalyst volume, where the liquid volume and the catalyst volume are in the same volumetric units. The water concentration is typically less than 200 wppm, and preferably less than 20 wppm, and more preferably less than 5 wppm.

The molar ratio of phenyl groups per alkyl group, which is often referred to as the phenyl/alkyl ratio, is a key operating variable for transalkylation because the equilibrium conversion of polyalkyl aromatics is a function of the phenyl/alkyl ratio. The numerator of this ratio is the number of moles of phenyl groups passing through the transalkylation zone during a specified period of time. The number of moles of phenyl groups is the sum of all phenyl groups, regardless of the compound in which the phenyl group happens to be. In the context of cumene production, for example, one mole of benzene, one mole of cumene, one mole of diisopropylbenzene (DIPB), and one mole of tri-isopropylbenzene (TIPB) each contribute one mole of phenyl group to the sum of phenyl groups. The denominator of this ratio is the number of moles of alkyl groups passing through the transalkylation zone during the same specified period of time. The number of moles of alkyl groups is the sum of all alkyl and alkenyl groups, regardless of the compound in which the alkyl or alkenyl group happens to be, except that paraffins are not included. Thus, in the production of cumene (isopropylbenzene), the number of moles of propyl groups is the sum of all propyl and propenyl groups, regardless of the compound in which the propyl or propenyl group happens to be, but excluding paraffins. Paraffins, such as, propane, n-butane, isobutane, pentanes, and higher paraffins, are excluded from the computation of the number of moles of propyl groups. For example, one mole of propylene and one mole of cumene each contribute one mole of propyl group to the sum of propyl groups, whereas one mole of DIPB contributes two moles of propyl groups and one mole of TIPB contributes three moles of propyl groups. For cumene production, the phenyl/propyl ratio is generally from 8:1 to 1:1, and preferably from 6:1 to 3:1. Where the transalkylation feed consists of only benzene and DIPB, the phenyl/propyl ratio may be computed from the molar ratio of benzene per DIPB, which is referred to as the benzene/DIPB ratio, by using the mathematical formula, phenyl/propyl ratio=½×(benzene/DIPB ratio+1). This mathematical formula is sufficiently accurate as an approximation of the phenyl/propyl ratio when the cumene content or the TIPB content of the transalkylation feed is less than 1.0 vol.-%.

The transalkylation reaction zone may be operated and arranged in any manner that provides the desired operating conditions and the required contacting of reactants and catalyst. A single contacting stage in transalkylation is routinely used, in part because the transalkylation reactions are neither very exothermic nor very endothermic.

The transalkylation effluent stream contains not only the desired monoalkyl aromatic product (cumene) but also unreacted transalkylation reactants as well as transalkylation by-products. Of the transalkylation reactants, benzene is usually the most abundant, because in transalkylation benzene is generally present in a stoichiometric excess to the polyisopropylbenzenes. Diisopropylbenzenes (DIPB) in the transalkylation feed also are generally present in the transalkylation effluent stream because the DIPB conversion in transalkylation is limited by equilibrium to less than 100%. Higher polyalkylbenzenes such as triisopropylbenzenes (TIPB) and tetraisopropyl-benzenes also may be present in the transalkylation effluent, either as an unreacted transalkylation reactant or as a transalkylation by-product from the reaction of a polyalkylbenzene with another polyalkylbenzene rather than with benzene.

As mentioned previously, passing some of the transalkylation effluent stream to the alkylation reaction zone is an essential element of this invention. The portion of the transalkylation effluent stream that passes to the alkylation reaction zone is generally from about 5 to 100% of the transalkylation effluent stream, and preferably from about 70 to 100%. The portion of the transalkylation effluent stream that passes to the alkylation reaction zone is preferably an aliquot portion of the transalkylation effluent stream. As used herein, the term "aliquot portion of a stream" means a portion of the stream that has essentially the same composition as the stream.

The alkylation reaction zone feed stream contains not only components that exit the transalkylation reaction zone but also additional components that are injected into the transalkylation effluent stream. For instance, the alkylating agent (propylene) enters the transalkylation effluent stream between the transalkylation and alkylation reaction zones. In addition, if the quantity of alkylation substrate (benzene) in the transalkylation effluent is insufficient for the alkylation reaction zone or if the temperature in the alkylation reaction zone requires adjustment, then additional fresh or recycle benzene may be combined with the transalkylation effluent stream and passed to the alkylation reaction zone. Of course, as mentioned previously, if additional benzene is required for alkylation, then it may be preferable, subject to transalkylation space velocity constraints, for that benzene to be first passed through the transalkylation reaction zone, where a higher ratio of benzene per diisopropylbenzene and a higher ratio of phenyl groups per propyl groups would tend to increase diisopropylbenzene conversion. Finally, water may be added to the transalkylation effluent stream, because some alkylation catalysts benefit from operating at a higher concentration of water than transalkylation catalysts.

The alkylation reaction zone can operate over a broad range of operating conditions. The alkylation reaction zone is ordinarily operated to obtain an essentially complete conversion of the alkylating agent (propylene) to cumene, diisopropylbenzene, or heavier polyisopropylbenzenes. Propylene conversion is generally more than 99.5% and preferably more than 99.9%. Preferably, the operating conditions result in nearly equilibrium concentrations of cumene being produced in the alkylation reaction zone. The concentration of cumene is generally greater than 80% of the equilibrium concentration, and preferably greater than 95%. To help attain such a high cumene concentration, a stoichiometric excess of benzene over propylene is generally present in the alkylation reaction zone feed. The molar ratio of benzene per propylene is generally from 20:1 to 1:1, and preferably from 5:1 to 1:1. The preferred molar ratio of phenyl groups per propyl group in the alkylation reaction zone is from 5:1 to 1:1. Temperatures usually range from about 210° F. (99° C.) to about the critical temperature of the alkylation substrate, which is about 554° F. (290° C.) for benzene and may be 889° F. (475° C.) or even higher for heavier alkylation substrates. Temperatures are preferably in the range of about 250 to 350° F. (121 to 177° C.) and more preferably in the range of about 270 to 350° F. (132 to 177° C.). Pressures can also vary within a wide range of from about 1 atmosphere to about 130 atmospheres. Because liquid phase conditions are generally preferred within the alkylation reaction zone, the pressure should be sufficient to maintain the benzene in a liquid phase and will typically fall in a range of from 10 to 50 atmospheres. The benzene liquid hourly space velocity (LHSV) is generally from about 0.5 to 50 hr$^{-1}$, and preferably from about 1 to 10 hr$^{-1}$. The water concentration in the alkylation reaction zone is generally greater than 50 wppm, but may be over 500 wppm, depending on the particular catalyst. The propylene concentration in the alkylation reaction zone is generally less than 12 wt-% and preferably less than 6 wt-% in order to minimize formation of alkylation by-products.

This invention is typically suitable to the case where the stream containing the alkylating agent contains non-alkylating materials, and preferably with low concentrations of the non-alkylating materials. For example, in a cumene process the propylene-containing stream commonly contains some propane. This invention is particularly applicable where the propylene stream of a cumene process contains from 0 to about 50 wt-% propane.

A catalyst promotes the initial alkylation of the alkylation substrate in the alkylation reaction zone. A wide variety of catalysts can be used in the alkylation reaction zone. Suitable catalysts for use in the alkylation reaction zone will comprise any catalyst that is not deactivated rapidly as a consequence of including heavies in the alkylation reaction zone feed. In addition, the presence of heavies should not have a deleterious effect on the approach to equilibrium cumene concentrations in the alkylation reaction zone. If polyisopropylbenzenes are present in the alkylation reaction zone feed, those with fewer propyl groups are preferred, as are low concentrations of any polyisopropylbenzenes that are present. Preferably, the concentration of polyisopropylbenzenes is less than 5 wt-% of the alkylation reaction zone feed. Also, the presence of cumene in the alkylation feed should not have a significant adverse effect on the production of cumene in the alkylation reaction zone.

The preferred alkylation catalyst for use in this invention is a zeolitic catalyst. Suitable zeolites include zeolite Y, zeolite beta, ZSM-5, PSH-3, MCM-22, MCM-36, MCM-49, and MCM-56. Zeolite Y is described in U.S. Pat. No. 3,130,007. A preferred zeolite Y is essentially free of residual non-H$^+$ cations, by which it is meant that the non-H$^+$ cation content of the zeolite Y is less than 200 wppm calculated as NH$_3$ equivalents. Thus, the number of H$^+$ acid sites in the preferred zeolite Y is maximized. Zeolite beta is described in U.S. Pat. No. 3,308,069 and Re U.S. Pat. No. 28,341. The topology of zeolite beta and the three zeolite beta polytypes are described in the article by Higgins, et al., in Zeolites, Vol. 8, November 1988, starting at page 446; and in the letter by M. M. J. Treacy et al., in Nature, Vol. 332, March 17, 1988, starting at page 249. Suitable zeolite betas include, but are not limited to, the naturally occurring is mixture of the three polytypes, any one of the three polytypes, or any combination of the three polytypes. The use of zeolite beta in alkylation and transalkylation is disclosed in U.S. Pat. Nos. 4,891,458 and 5,081,323, and the use of pristine zeolite beta in alkylation is disclosed in European Patent EP 432,814 B1. Suitable zeolite betas include, but are not limited to, pristine zeolite beta in which the H$^+$ ion has at least partially replaced the contained metal cation, as disclosed in European Patent EP 432,814 B1; and zeolite beta into which certain quantities of alkaline, alkaline-earth, or metallic cations have been introduced by ion exchange, as disclosed in U.S. Pat. No. 5,672,799. Various modifications of zeolite beta are also suitable for use in this invention. Suitable modified zeolite betas include, but are not limited to, zeolite beta which has been modified by steam treatment and ammonium ion treatment, as disclosed in U.S. Pat. No. 5,522,984; and zeolite beta in which the H$^+$ ion has at least partially replaced the contained metal cation, with the zeolite beta being modified by isomorphous substitution of aluminum by boron, gallium, or iron, as disclosed in European Patent EP 432,814 B1. Suitable zeolites for use in this invention also include zeolites that are synthesized by modified preparation methods, such as, but not limited to, a preparation method comprising forming a reaction mixture comprising water, a source of silicon dioxide, a source of fluoride ions, a source of tetraethylammonium cations, and, optionally, a source of an oxide of a trivalent element, as disclosed in PCT International Publication Number WO 97/33830. ZSM-5 is described in U.S. Pat. No. 3,702,886 and Re U.S. Pat. No. 29,948. PSH-3 is disclosed in U.S. Pat. No. 4,439,409. MCM-22 is disclosed in U.S. Pat. Nos. 4,954,325 and 4,992,606, and its structure is described in the article in Science, Vol. 264, pp.1910–1913 (Jun. 24, 1994). U.S. Pat. Nos. 5,077,445; 5,334,795; and 5,600,048 describe the use of MCM-22 to produce alkylaromatics. MCM-36 is disclosed in U.S. Pat. Nos. 5,250,277 and 5,292,698. The use of a catalyst comprising MCM-36 to produce alkylaromatics such as ethylbenzene is disclosed in U.S. Pat. Nos. 5,258,565 and 5,600,048. The synthesis of MCM-49 is described in U.S. Pat. No. 5,323,575, and the use of MCM-49 to produce alkylaromatics including the liquid phase production of ethylbenzene is described in U.S. Pat. Nos. 5,371,370; 5,493,065; and 5,600,048. MCM-56 is disclosed in U.S. Pat. No. 5,362,697. The use of MCM-56 to produce ethylbenzene and other alkylaromatics is disclosed in U.S. Pat. Nos. 5,453,554 and 5,600,048.

A preferred zeolite beta for use in alkylation in this invention is disclosed in U.S. Pat. No. 5,723,710, the teachings of which are incorporated herein by reference. This preferred zeolite is a surface-modified zeolite beta which results from acid washing of a templated native zeolite beta. That is, the formation of the surface-modified zeolite beta starts with a templated beta where the template is, for example, a tetraalkylammonium salt, such as tetraethylammonium salt. It is critical to-acid wash a templated zeolite beta in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, and so forth. For example, a weak, 0.01 molar nitric acid may is be used in conjunction with ammonium nitrate to perform the acid wash, although substantially higher concentrations, up to about 20 weight percent nitric acid, are preferred. Nitric acid is a preferred acid since it is a non-complexing acid and therefore does not encourage dealumination. Treatment of the templated zeolite beta with strong acid may be effected over the temperature range between about 20° C. (68° F.) up to about 125° C. (257° F.). It is important that acid washing be done under conditions not so severe as to effect dealumination.

The time over which acid washing is conducted in preparing the preferred zeolite is quite temperature dependent. It is critical in the formation of the surface-modified zeolite beta that there be no significant bulk dealumination of the zeolite. Thus, as a general statement it can be said that acid washing should be done for a time insufficient to effect dealumination. For example, using 0.01 molar nitric acid and circa 40% ammonium nitrate at 70° C. (158° F.), contact times of 2–3 hours are found adequate to modify the environment of surface aluminum without causing significant bulk dealumination. Using circa 15% nitric acid with ammonium nitrate to treat a circa 25 weight percent slurry at 85° C. (185° F.), a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550–700° C. (1022–1292° F.). Calcination conditions are well known in the art and need not be elaborated upon here. It also needs to be mentioned that powdered zeolite itself is not usually used as the alkylation catalyst. Therefore, in the more usual case after the templated zeolite beta is acid washed it is mixed with a conventional binder, extruded, and the extrudate is ultimately calcined. But the critical portion of the preparation of the preferred zeolite is the acid wash of the templated beta according to the foregoing description. Acid washing a calcined (i.e., non-templated) zeolite beta does not produce the surface-modified material of the preferred zeolite.

It has been found that after treatment as described above the surface aluminum atoms are chemically modified. It has been hypothesized that the modification is in the form of replacement of strong acid sites at the catalyst surface by weaker acid sites. What has been definitely observed is that the surface aluminums of the preferred modified zeolite beta have 2p binding energies as measured by x-ray photoelectron spectroscopy of at least 74.8 electron volts.

As mentioned previously, the zeolite will usually be used in combination with a refractory inorganic oxide binder. Preferred binders are alumina and silica. Preferred alkylation catalysts include zeolite Y with an alumina or silica binder, and zeolite beta or the previously-described surface-modified zeolite beta with an alumina or silica binder. The zeolite will usually be present in an amount of at least 50 wt-% of the catalyst, and preferably in an amount of at least 70 wt-% of the catalyst. This process is useful for any arrangement of transalkylation reaction zone and alkylation reaction zone wherein the effluent of the former is passed to the latter. However, it has been found that a beta zeolite or a Y type zeolite contained in an alumina binder will perform very well when used in both the alkylation reaction zone and the transalkylation reaction zone. Therefore, both reaction zones may use the same catalyst. Accordingly, in a preferred embodiment of this invention for cumene production, beta zeolite is used as the catalyst in both the alkylation and transalkylation zones.

There is no requirement, however, that the alkylation reaction zone and the transalkylation reaction zone use the same catalyst. For example, an embodiment for cumene production uses Y zeolite as the transalkylation catalyst and beta zeolite as the alkylation catalyst. This combination of Y zeolite for transalkylation and beta zeolite for alkylation may generally be used for producing cumene when the molar ratio of phenyl groups per isopropyl group in the alkylation zone is less than 3:1, the transalkylation temperature is from about 250 to about 350° F. (121 to 177° C.), and the alkylation temperature is from about 250 to about 350° F. (121 to 177° C.).

There is also no requirement that the transalkylation reaction zone and the alkylation reaction zone be in separate vessels. However, it is believed that an alkylation reaction zone and a transalkylation reaction zone will require less capital expense and be less mechanically complex when both are in a single, common reaction vessel. Therefore, in the preferred embodiment of this invention, both reaction zones are in the same reaction vessel.

The alkylation reaction zone may be operated and arranged in any manner that provides the desired operating temperatures and number of contacting stages. Multiple contacting stages in the alkylation reaction zone are routinely used to provide cooling by the staged addition of reactants and/or cooled reactor effluent quench to multiple beds of alkylation catalyst. The multiple injection of the reactants or quench serves to cool the stages between alkylation catalyst beds, to provide temperature control, and to reduce the concentration of alkylating agent (e.g., propylene).

Ordinarily, the alkylation catalyst is arranged in multiple beds to permit series flow of the alkylation substrate (e.g., benzene) and parallel flow interbed injection of the alkylating agent (e.g., propylene). Thus, in the usual situation, benzene is provided in a molar excess to the olefin, all of the benzene that is provided to the multiple beds is introduced into the first bed, and the effluent of each of the beds flows to the next bed in the series. In this way, unreacted benzene from each bed is made available to react in the next bed in the series. However, where the alkylation catalyst is arranged in multiple beds, the alkylation substrate can also be injected between beds of alkylation catalyst. Multiple beds of alkylation catalyst means two or more beds of alkylation catalyst. In theory, there is no upper limit as to the number of alkylation catalyst beds, but in practice the maximum number of beds of alkylation catalyst is determined by a number of factors, including the ability to distribute flow in each bed uniformly, the ability to inject alkylating agent and/or alkylation substrate to each bed evenly, the exothermic temperature rise in each bed, and the clearance and/or access required to assemble and maintain the mechanical equipment associated with each bed. A typical alkylation unit usually has 4 or 6 alkylation catalyst beds, but it is also possible to have as many as 10, 20, or more alkylation catalyst beds.

In this invention, the portion of the transalkylation effluent stream that passes to a multibed alkylation reaction zone is itself divided into sub-portions, preferably aliquot sub-portions. As used herein, the term "aliquot sub-portion of a portion" means a sub-portion of the portion that has essentially the same composition as the portion. One sub-portion of the transalkylation effluent stream passes to the first bed in the series, and a second sub-portion is passed to another bed in the series. In the case where there are only two alkylation catalyst beds, between about 0 and about 99% of the portion of the transalkylation effluent stream that passes to the alkylation reaction zone passes to the first bed in the series, and the remainder, i.e., between about 1 and about 100% of the transalkylation effluent stream that passes to the alkylation reaction zone, passes to the second alkylation bed. Where there are three or more alkylation catalyst beds, between about 0 and about 99% of the portion of the transalkylation effluent stream that passes to the alkylation reaction zone passes to the first bed in the series, and for any other alkylation bed in the series, between about 0 and about 100% of the portion of the transalkylation effluent stream that passes to the alkylation reaction zone passes to that other bed in the series. Thus, where a portion of the transalkylation effluent passes stage-wise to an alkylation reaction zone having four alkylation catalyst beds, numerous possibilities for the distribution of the portions of the transalkylation effluent exist. One possibility is 25% to each of the four beds. A second possible distribution is 10% to the first bed, 40% to the second bed, 0% to the third bed, and 50% to the fourth bed. A third possible distribution is 30% to the first bed, 10% to the second bed, 60% to the third bed, and 0% to the fourth bed. Because the transalkylation effluent is generally at a temperature that is less than the effluent temperature of each alkylation bed, the transalkylation effluent that is injected between the alkylation beds can provide not only multiple injection of reactants but also quench for the alkylation catalyst beds.

Where alkylation substrate is injected directly to one or more beds of alkylation catalyst, there are numerous possible distributions for the portions of the alkylation substrate. In the case of only two alkylation catalyst beds, between about 0 and about 100% of the alkylation substrate that passes directly to the alkylation reaction zone passes to the first bed in the series, and the remainder, i.e., between about 0 and about 100% of the alkylation substrate that passes to the alkylation reaction zone, passes to the second alkylation bed. In the case of three or more alkylation catalyst beds, between about 0 and about 100% of the portion of the alkylation substrate that passes to the alkylation reaction zone passes to the first bed in the series, and for any other alkylation bed in the series, between about 0 and about 100% of the portion of the alkylation substrate that passes to the alkylation reaction zone passes to that other bed in the series. Where there are four alkylation catalyst beds in the alkylation reaction zone, some of the possible distributions of the portions of the alkylation substrate are: 25% to each of the four beds; 0% to the first bed, 20% to the second bed, 30% to the second bed, and 50% to the fourth bed; 50% to the first bed, 50% to the second bed, 0% to the third bed, and 0% to the fourth bed; 100% to the first bed, and 0% to each of the second, third, and fourth beds.

Many combinations of transalkylation effluent distributions and alkylation substrate distributions to the alkylation beds are possible, and the description of possible combinations that are described herein is not intended to limit the scope of the invention as set forth in the claims. For example, for a given number a alkylation catalyst beds, any of the individual distributions of transalkylation effluent described herein may be combined with any of the individual distributions of alkylation substrate described herein. One example combination comprises directing to each alkylation bed essentially equal portions of the transalkylation effluent that passes to the alkylation reaction zone while directing to each alkylation bed essentially equal portions of the alkylation substrate that passes directly to the alkylation reaction zone. However, particular combinations of transalkylation effluent and alkylation substrate distributions are believed to decrease the formation of heavies by-products such as diphenylpropane and alkylated diphenylpropanes. Particularly desirable combinations of transalkylation effluent distributions and alkylation substrate distributions to a series of alkylation beds include those in which the first bed receives from about 0 to about 50% of the transalkylation effluent that passes to the alkylation is reaction zone, and about 50 to about 100% of the alkylation substrate that passes directly to the alkylation reaction zone. Other desirable combinations of distributions are those in which, compared to the bed that is immediately upstream, each bed in the series receives a larger portion of the transalkylation effluent that passes to the alkylation reaction zone and a smaller portion of the alkylation substrate that passes directly to the alkylation reaction zone.

Where the alkylation reaction zone contains separate alkylation catalyst beds, the separate beds may be arranged in a single vessel or in multiple vessels. In practicing this invention with multiple alkylation catalyst beds, a common vessel may contain the transalkylation reaction zone and one or more alkylation reaction catalyst beds. However, for very large units separate vessels for the transalkylation catalyst bed and for one or more alkylation catalyst beds may be more advantageous.

The alkylation effluent generally is a mixture of the desired monoalkyl aromatic product with a wide variety of undesired by-products. For example, in the alkylation of benzene with propylene to produce cumene, the reaction zone can produce diisopropylbenzenes, triisopropylbenzenes, tetraisopropylbenzenes, heavier polyisopropylbenzenes, and other heavies such as diphenylpropane in addition to other propylene condensation by-products. Transalkylation also yields additional alkyl aromatic by-products, which in this invention can be alkylated in the alkylation reaction zone to produce still other by-products. Generally, the alkylation effluent stream also contains a substantial amount of unreacted aromatic substrate (benzene), because aromatic substrate is ordinarily present in a stoichiometric excess in both transalkylation and alkylation. Therefore, a number of separation stages are needed to separate the desired aromatic product from the by-products and the unreacted aromatic substrate.

A number of combinations of columns and separators can be used to recover the desired isopropyl aromatic product and to produce recycle streams of aromatic substrate and polyisopropyl aromatics for transalkylation. Typically, a first column separates light paraffins that entered the process with the alkylating agent and that passed through the alkylation reaction zone without reacting. A second column separates the aromatic substrate from the remaining heavier components of the alkylation effluent stream. Alternatively, the order of these first two columns may be reversed, in which case a low alkane (e.g., propane) content of the alkylating agent stream (e.g., propylene-containing stream) is preferred. One or more additional separation columns separate the desired aromatic product from by-product streams that contain lighter or heavier by-products. Heavies by-products that are not suitable or are not desirable for transalkylation are usually rejected from the process.

In a preferred embodiment of this invention, the effluent of any alkylation catalyst bed is divided into at least two aliquot portions. In this embodiment, one aliquot portion of an alkylation catalyst bed effluent passes to another alkylation catalyst bed in the series of alkylation beds that is downstream in relation to the alkylation catalyst bed from which the effluent is withdrawn, except if this aliquot portion is withdrawn from the last alkylation catalyst bed in the series, in which case this aliquot portion passes to the aforementioned columns and separators to recover the desired isopropyl aromatic product and to produce recycle streams. In addition, in this embodiment at least one other aliquot portion of the alkylation catalyst bed effluent is recycled either to the alkylation catalyst bed from which the effluent is withdrawn or to another alkylation catalyst bed in the series of alkylation beds that is upstream in relation to the alkylation catalyst bed from which the effluent it is withdrawn. An aliquot portion that is introduced into an alkylation catalyst bed may be cooled and is preferably introduced into the inlet of the alkylation catalyst bed. In this embodiment, an aliquot portion of the transalkylation effluent may pass to one of the beds, or a plurality of aliquot portions of transalkylation effluent may pass to a plurality of beds, including beds to which alkylation effluent is introduced. For a bed into which an alkylation effluent portion is recycled and to which transalkylation effluent is also passed, the flow rate of the alkylation effluent portion relative to that of the transalkylation effluent portion is selected depending on several factors, including the inlet temperature and the maximum temperature in the bed, which can in turn influence the deactivation rate of the catalyst, the production of desired product, and the production of byproducts in the bed. For the production of cumene, the inlet temperature of such a bed is generally from about 250 to about 270° F. (121 to 132° C.), and the maximum temperature of such a bed is generally from about 300 to about 350° F. (149 to 177° C.).

An example of recycling alkylation effluent in an embodiment of the present invention having an alkylation reaction zone comprising a single alkylation reactor containing two alkylation catalyst beds in series is passing one aliquot portion of the effluent from the second alkylation bed to the columns and separators for product recovery while recycling one or more other portions to the first alkylation bed, the second alkylation bed, or both. In another example, wherein an alkylation reaction zone has two alkylation reactors in a series flow arrangement and wherein each reactor contains two catalyst beds in a series flow arrangement, an aliquot portion of the effluent of the downstream bed of the downstream reactor may be recycled to the upstream bed of the upstream reactor, to the upstream bed of the downstream reactor, or to both upstream beds. Similarly, an aliquot portion of the transalkylation effluent may pass to the upstream bed of the upstream reactor, to the upstream bed of the downstream reactor, or to both upstream beds.

The operation of this invention and of an arrangement of separation zones to recover product and to produce recycle streams can be better understood by referring to FIG. 1. FIG. 1 schematically illustrates the major equipment used in performing the process of this invention for the production of cumene. In the process, fresh benzene feed flows through a line 28 and mixes with a stream in a line 84 that contains recycle benzene as well as recycle diisopropylbenzenes and triisopropylbenzenes. The mixture flows through a line 86 and enters a bed 12 of zeolitic transalkylation catalyst. A vessel 10 houses the transalkylation bed 12. After contact with the catalyst in bed 12, the -transalkylation zone effluent from bed 12 exits from vessel 10 via line 11, and splits into two portions. One portion of the transalkylation effluent flows through line 13, receives propylene via lines 32, 34, and 42, and enters by line 17 into an alkylation bed 14 of zeolitic alkylation catalyst. A vessel 30 houses alkylation bed 14 and an additional alkylation bed 16. Effluent from bed 14 receives propylene via lines 32, 34, and 38, and enters bed 16 which contains zeolitic alkylation catalyst. Alkylation bed 16 effluent flows from vessel 30 via line 31 and combines with the other portion of the transalkylation effluent flowing in line 15. The combined effluents flow through lines 33 and 50 to a vessel 20, which contains another series of alkylation beds 18, 22, 24, and 26 which all contain zeolitic alkylation catalyst. Alkylation bed 16 effluent enters bed 18, bed 18 effluent enters bed 22, bed 22 effluent enters bed 24, and bed 24 effluent enters bed 26. Incidentally, water (not shown) may be injected into any, some, or all of the alkylation beds. Lines 32 and 36 supply propylene for the alkylation beds in the vessel 20. The propylene for bed 18 flows through lines 44, 46, 48, and 50 and enters vessel 20 upstream of bed 18. Similarly, propylene for bed 22 flows through lines 44, 46, and 52; propylene for bed 24 flows through lines 44 and 54; and propylene for bed 26 flows through line 56. Alkylation zone effluent from alkylation bed 26 flows from vessel 20 via a line 58.

The line 58 from vessel 20 supplies alkylation zone effluent to a benzene column 40. Although not shown in FIG. 1, line 58 may optionally supply alkylation zone effluent to each alkylation bed 14, 16, 18, 22, 24, and 26 by recycling to a point upstream of each bed. From benzene column 40 are withdrawn a fraction containing benzene and light hydrocarbons in a line 62 and a bottom stream containing higher boiling hydrocarbons in a line 64. Line 62 passes the fraction to a depropanizer 60. Although not shown in the FIG. 1, a portion of the fraction in the line 62 may optionally be recycled to a point upstream of alkylation bed 14 in vessel 10 to provide additional benzene with a relatively high water concentration for the alkylation reaction zone.

Depropanizer 60 recovers in a line 68 a purified benzene stream having a relatively low water concentration. A line 66 passes an overhead stream containing propane and water from the depropanizer 60. The line 64 carries the bottom stream of the benzene column 40 to a cumene column 70. A line 72 recovers a cumene product overhead, and a line 74 transfers a bottoms stream to a heavies column 80 for the recovery of diisopropylbenzene and triisopropylbenzene via a line 82, a lighter boiling material via a line 78, and heavies via a line 76. A purified stream of diisopropylbenzene and triisopropylbenzene returns as recycle via the line 82, combines with benzene in the line 68, and the combination is carried by the lines 84 and 86 to the transalkylation catalyst bed 12 in the vessel 10. As described previously, the effluent from the transalkylation bed 12 flows through vessel 10 to the top of alkylation catalyst bed 14.

Subject to transalkylation space velocity considerations, passing all of the recycle benzene that flows through the line 68 to transalkylation reactor 12 is advantageous in comparison with diverting a portion of the recycle benzene in line 68 around the transalkylation reactor 12 and then passing that portion directly to alkylation bed 12. This advantage arises because any phenyl groups passed to transalkylation reactor 12 ultimately pass to the alkylation beds 14, 16, 18, 22, 24, and 26. Therefore, passing all of the recycle benzene to the transalkylation reactor increases the phenyl/propyl ratio in the transalkylation reactor without decreasing the phenyl/propyl ratio in the alkylation beds.

COMPARATIVE EXAMPLES I AND II

Figure 2:
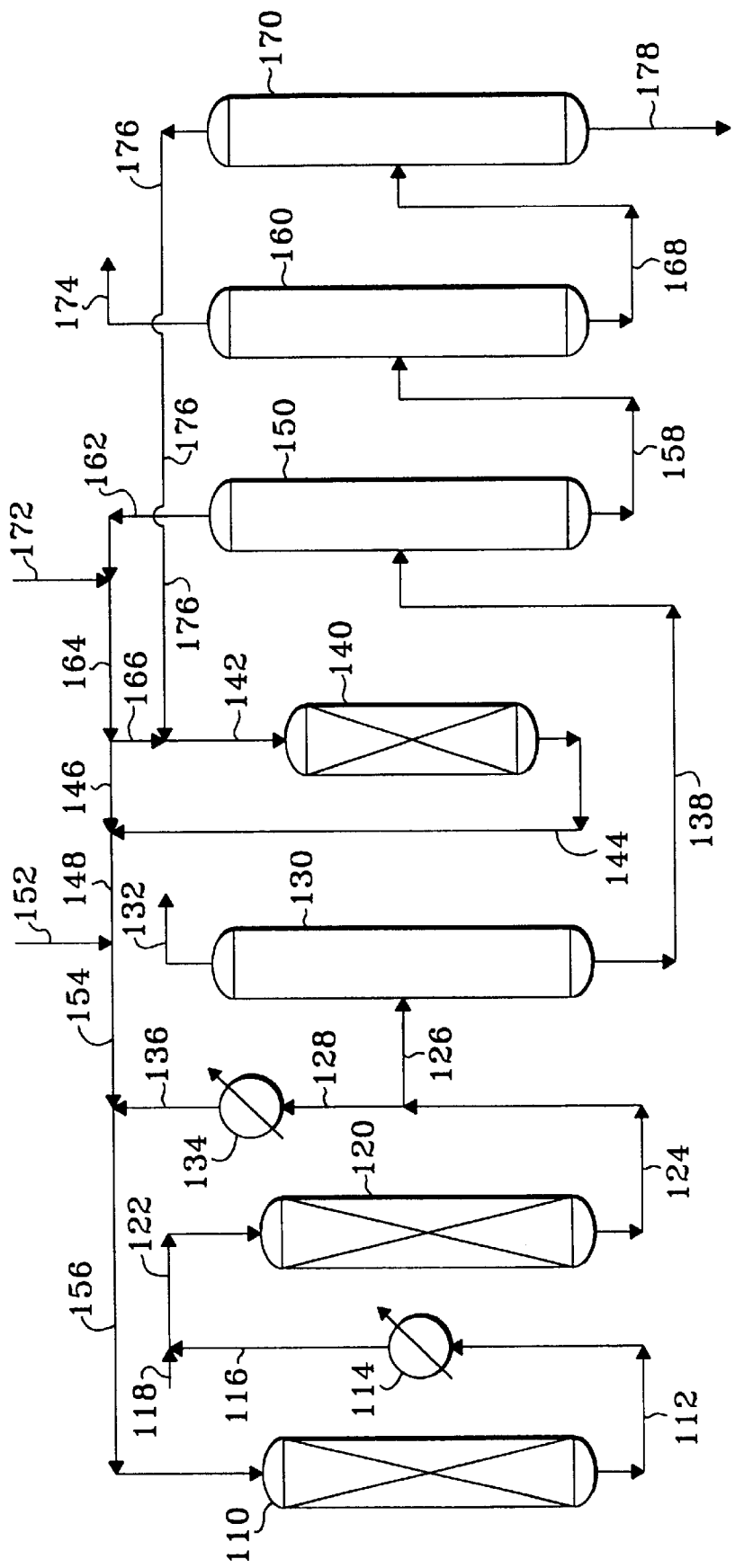

These comparative examples illustrate, on the one hand, not passing and, on the other hand, passing the entire effluent of a transalkylation reactor to the first of two alkylation reactors in a series flow arrangement. Both Examples I and II are based on plant operations and laboratory experiments. In describing these examples, reference is made to FIG. 2, which shows the flow scheme for Example II. The flow scheme for Example I is the same as that shown in FIG. 2, except for those changes that are described hereinafter. In FIG. 2, valves, pumps, heaters, instruments, and heat exchangers other than those necessary for an understanding and appreciation of the invention have been omitted.

Referring now to FIG. 2, makeup benzene enters the process via a line 172 and combines with recycle benzene in a line 162 from the overhead of a benzene column 150. The combined stream of makeup and recycle benzene flows through a line 164, and then divides into two portions. One portion flows through a line 166 and combines with recycle diisopropylbenzene flowing in a line 176 from the overhead of a polypropylbenzene column 170. The combined stream of benzene and recycle diisopropylbenzene flows through a line 142 and enters a transalkylation reactor 140 containing a beta zeolite transalkylation catalyst. After contacting the transalkylation catalyst, a transalkylation effluent leaves the transalkylation reactor 140 through a line 144 and combines with the second portion of recycle benzene flowing in a line 146, which is used to control the phenyl to propyl ratio in the alkylation reactors.

The combined stream of transalkylation effluent and benzene flows through a line 148, combines with makeup propylene entering through a line 152, and flows through a line 154. A cooled portion of alkylation effluent flowing through a line 136 combines with the stream flowing in the line 154, and the combined feed flows through a line 156 to a first alkylation reactor 110. Alkylation reactor 110 contains a single bed of zeolite beta alkylation catalyst. After contacting the alkylation catalyst, a first alkylation effluent stream leaves alkylation reactor 110 through a line 112. Cooler 114 cools the first alkylation effluent, which after cooling flows through a line 116 and a line 122 and enters a second alkylation reactor 120. Additional propylene enters the process through a line 118, combines with the cooled first alkylation effluent, flows through the line 122, and enters the second alkylation reactor 120. Second alkylation reactor 120 contains a single bed of beta zeolite alkylation catalyst. After contacting the catalyst in the alkylation reactor 120, a second alkylation effluent leaves the reactor 120 through a line 124.

The second alkylation effluent divides into two portions. One portion flows through a line 128, is cooled in a cooler 134, and flows through the line 136 to combine with the stream flowing through the line 154 as described previously. This portion controls the propylene concentration and mass flow in the alkylation reactors. The other portion of the second alkylation effluent flows through a line 126 and enters a depropanizer 130. The depropanizer 130 removes propane and other light ends which may have entered the process with the makeup propylene streams 152 and 118. A line 132 carries the depropanizer overhead stream containing this propane and these light ends from the process. A depropanizer bottoms stream flows through a line 138 to the benzene column 150.

Benzene column 150 removes recycle benzene, which is carried overhead through the line 162 as described previously. A benzene column bottoms stream flows through a line 158 to a cumene column 160. The cumene column 160 produces an overhead stream containing the product cumene that is recovered from the process through a line 174. A cumene column bottoms stream flows through a line 168 to the polypropylbenzene column 170, which removes recycle diisopropylbenzene through an overhead line 176 as described previously. A polypropylbenzene column bottoms stream removes polypropylbenzenes heavier than diisopropylbenzene and other heavies through a line 178.

Table 1 shows the operating conditions and yields for the two examples. In Table 1, the "effluent/feed recycle" ratio is computed by dividing the recycle effluent flow rate in the line 136 by the sum of the flow rates of the streams in lines 146, 152, 118, and, for Example II only, 144. Overall liquid hourly space velocity (LHSV) is defined as the liquid flow rate of transalkylation feed in the line 142 divided by the transalkylation catalyst volume in the transalkylation reactor 140. The ratio "delta nPB/delta cumene" represents the quotient of the change in n-propylbenzene (nPB) concentration across a reactor expressed in wppm divided by the change in cumene concentration across the same reactor expressed in units of weight fraction. Accordingly, for transalkylation the "delta nPB/delta cumene" ratio represents the difference in nPB concentrations between the streams in line 142 and 144 divided by the difference in cumene concentrations between the streams 142 and 144. Similarly, for alkylation the "delta nPB/delta cumene" ratio represents the difference in nPB concentrations between the streams 156 and 124 divided by the difference in cumene concentrations between the streams 156 and 124.

COMPARATIVE EXAMPLE I

The flow scheme for Example I is the same as that shown in FIG. 2, except that the innovation of this invention is not employed. Specifically, the flow scheme for Example I is that shown in FIG. 2, except that the transalkylation effluent line 144 is not routed to the junction of lines 146 and 148 but rather is routed to the depropanizer bottoms line 138. Accordingly, no transalkylation effluent passes without separation to the alkylation reactors 110 and 120. The flow through transalkylation and alkylation can thus be considered as being in parallel.

A catalyst containing surface-modified zeolite beta that was prepared as previously described herein was loaded into alkylation reactors 110 and 120 and also into transalkylation reactor 140, and the reactors were operated according to the Example I parallel flow scheme for approximately 187 days-on-stream. During these first approximately 187 days-on-stream, the targeted transalkylation conditions included a DIPB LHSV of about 0.55 $hr^{-1}$ and a benzene/DIPB molar ratio of about 4, in order to attain a targeted DIPB conversion of about 40%. Meanwhile, the targeted alkylation conditions included a propylene LHSV of about 0.5 $hr.^{-1}$, an effluent/feed ratio of 3, and benzene/propylene molar ratio of from about 3 to about 4, in order to attain a targeted propylene conversion of about 100%. The last four days, that is approximately days-on-stream 184–187, of this standard parallel operation were averaged to produce the operating conditions and yields under the column heading "Example I" in Table 1.

Table 1 shows the operating conditions and yields for the parallel flow arrangement of transalkylation and alkylation of Example I. 291 mass units of diisopropylbenzene were produced in alkylation and the diisopropylbenzene conversion in transalkylation was 35.2%. The delta nPB/delta cumene ratio was 188 for alkylation and 394 for transalkylation.

COMPARATIVE EXAMPLE II

The flow scheme for Example II is substantially that shown in FIG. 2. Example II shows the effect of the innovative series flow arrangement for transalkylation and alkylation on cumene yield, formation of n-propylbenzene, and alkylation catalyst deactivation rate.

After approximately 187 days-on-stream, the flow scheme was switched from Example I to Example II. During approximately days-on-stream 188 to 194, the new flow scheme was allowed to line out. A slight decrease in water concentration in the alkylation reactors of approximately 10–20 ppm was observed. The next six days-on-stream, that is approximately days-on-stream 195 to 200, of the innovative series operation were averaged to produce the operating conditions and yields under the column heading "Example II" in Table 1.

For the series flow arrangement of Example II, Table 1 shows 213 mass units of diisopropylbenzene were produced in the alkylation reactors, and diisopropylbenzene conversion in the transalkylation reactors was 32.0%. The delta nPB/delta cumene ratio was 201 for alkylation and 388 for transalkylation. The overall cumene yield recovered through the line 174 was 98.7–99.3%.

One of the principal advantages of the series flow arrangement of Example II, as opposed to the parallel flow arrangement of Example I, is a decrease in the formation of diisopropylbenzene (DIPB) in the alkylation reactors 110 and 120. Only 213 mass units of DIPB were produced in alkylation in Example II, whereas 291 mass units of DIPB were produced in alkylation in Example I. It is believed that the explanation for the decreased DIPB formation in alkylation in Example II is the inhibiting effect of the DIPB in the transalkylation effluent which, when passed to the alkylation reactors 110 and 120, shifts the equilibrium away from further DIPB formation.

This decrease in DIPB formation in alkylation has important economic consequences, because it reduces the capital and operating costs associated with recycling benzene in a commercial alkylation-transalkylation process that uses this invention. As fewer moles of DIPB are formed in alkylation, fewer moles of DIPB need to be passed to and converted in transalkylation. Assuming a constant phenyl/propyl ratio in transalkylation, this in turn means that fewer moles of benzene need to be circulated to transalkylation, and hence the cost of equipment and utilities for circulating benzene can be significantly decreased.

It is evident that a decrease in DIPB formation in alkylation provides yet another important economic consequence, namely a reduction in the n-propylbenzene (nPB) content of the cumene product. As fewer moles of DIPB are formed in alkylation, fewer moles of DIPB need to be converted in transalkylation, and hence fewer moles of cumene are produced in transalkylation. Assuming a fixed total amount of cumene is produced in alkylation and transalkylation, as fewer moles of cumene are produced in transalkylation, more moles of cumene are produced in alkylation. Significantly, producing one mole of cumene in alkylation tends on average to form about half as much n-propylbenzene as producing one mole of cumene in transalkylation, as evidenced by the delta nPB/delta cumene ratio for alkylation being about one-half of the delta nPB/delta cumene ratio for alkylation. Therefore, decreasing DIPB formation in alkylation should help produce a cumene product having lower nPB impurity. Paradoxically, the data in Table I seems to show a slightly higher nPB content in the cumene product for Example II (237 wppm) as compared to Example 1 (234 wppm). However, it is believed that a reduction in nPB content nevertheless occurred, although masked by the experimental uncertainty in measuring the amount and concentration of nPB.

Another advantage of the series flow arrangement of Example II that is indicated by the results in Table 1 is that it is more likely than not that the series flow arrangement of Example II can be operated without rapid deactivation of the catalyst in alkylation reactors 110 and 120. This conclusion is surprising and unexpected, because persons of ordinary skill in the art had previously expected that series flow was impractical for the reason that the alkylation catalyst would become rapidly deactivated by polyalkylbenzenes heavier than DIPB, such as triisopropylbenzene (TIPB), and other by-products in the transalkylation effluent stream. Instead, the data from Examples I and II indicate that it is likely that the alkylation catalyst life in a series flow arrangement can be comparable to the alkylation catalyst life in a parallel flow arrangement, and hence will be sufficiently lengthy for suitable commercial operation.

One indication that the alkylation catalyst life in a series flow arrangement may be as suitable for commercial purposes as the alkylation catalyst life in a parallel flow arrangement comes from the surprising observation that the net rate of generation of diisopropylbenzene (DIPB) in series flow (Example II) is less than that in parallel flow (Example I). In parallel flow during days-on-stream 184 to 187, the DIPB production in alkylation (291 mass units) was approximately balanced by the DIPB conversion in transalkylation (35.2%), resulting in a net rate of DIPB generation of approximately zero. In contrast, during the initial, line-out days-on-stream 188 to 194 of series flow, DIPB production in alkylation was observed to be less than 291 mass units, and in order to compensate for the decrease in DIPB production in alkylation, transalkylation conditions were adjusted to decrease DIPB conversion in transalkylation. However, DIPB conversion in transalkylation was not decreased sufficiently during days-on-stream 188 to 194 for an approximate balance in net DIPB generation to be attained.

Not only was an approximate balance in net DIPB generation not attained during the lineout days-on-stream 188 to 194, it was also not attained during days-on-stream 195 to

200. The averaged data from days-on-stream 195 to 200 are presented as Example II in Table 1 and show DIPB production in alkylation was 213 mass units of DIPB, which is 78 mass units of DIPB less than in Example I. DIPB conversion in transalkylation, on the other hand, was 32.0% in Example II, which is only 3.2%-points less than in Example I. If DIPB production in alkylation in Example II had remained the same as that in Example I, then this rather small 3.2%-points decrease in DIPB conversion in transalkylation would have decreased by approximately 22 mass units the amount of DIPB converted in transalkylation in Example II. Because Example I had been in approximate balance, the relatively large decrease in DIPB production in alkylation (78 mass units) in combination with the relatively small decrease in DIPB conversion in transalkylation (22 mass units) caused Example II to not be in balance. Consequently, in Example II, more DIPB was being converted in transalkylation than was being produced in alkylation, and the net generation of DIPB was not approximately zero but instead was negative, thereby decreasing the inventory of DIPB in the flow scheme.

At least two consequences could follow from the fact that in Example II the DIPB production in alkylation was less than the DIPB conversion in transalkylation. First, at a given transalkylation LHSV, the transalkylation conditions in Example II could have been changed in order to further decrease the DIPB conversion in transalkylation from 32.0% to, say, 26%, at which point Example II's net DIPB generation rate would have been approximately balanced. Second, rather than by further decreasing the DIPB conversion, approximate balance could have been achieved by maintaining the same DIPB conversion in transalkylation and by decreasing the transalkylation LHSV, which would have had the added benefit of decreasing the benzene recycle rate.

Either means of achieving approximate balance in Example II in the net DIPB generation rate—that is, either decreasing the DIPB conversion in transalkylation at a constant transalkylation LHSV as was done to a degree in Example II, or decreasing the transalkylation LHSV at a constant DIPB conversion—allows transalkylation temperatures to be decreased, which is an advantageous step that leads to desirable results. Lowering the transalkylation temperatures reduces the formation of n-propylbenzene in transalkylation. This would even further lower the transalkylation delta nPB/delta cumene ratio, which is already less in Example II as compared to Example I.

For a specified n-propylbenzene (nPB) content of the cumene product, of, say, 250 wppm, good use can be made of a reduction in n-propylbenzene formation in transalkylation by increasing n-propylbenzene formation in alkylation. An increase in n-propylbenzene formation in alkylation would be most readily effected by increasing alkylation reaction temperatures. An increase in alkylation reaction temperatures would decrease the catalyst deactivation rate in the alkylation reactors and consequently increase alkylation catalyst life. Thus, as a consequence of the series flow arrangement of Example I, the temperatures of alkylation reactors 110 and 120 could have been increased. Although that would have produced more n-propylbenzene in alkylation, that increase would have been offset by the observed decreased rate of n-propylbenzene formation in transalkylation. Consequently, the overall cumene product purity would remain the same, and the alkylation catalyst life would be expected to improve.

Another indication that a series flow arrangement may be operated in a manner to achieve a suitable alkylation catalyst life as that achieved in a parallel flow arrangement follows from the surprising observation that the net rate of generation of triisopropylbenzene (TIPB) in series flow (Example II) is greater than that in parallel flow (Example I). Although the TIPB data are not shown in Table 1, it is believed that the explanation for the increased net rate of generation of TIPB in Example II is the DIPB in the transalkylation effluent which, when passed to the alkylation reactors 110 and 120, is alkylated and produces more TIPB. A high concentration of TIPB or heavier polyisopropylbenzenes in alkylation reactors 110 and 120 is believed to accelerate somewhat the deactivation rate of the alkylation catalyst.

An ingenious change to the flow scheme shown in FIG. 2 can increase the life of the alkylation catalyst in the alkylation reactors 110 and 120 by decreasing the likelihood of catalyst deactivation caused by TIPB. In addition, this change can decrease the capital and operating costs associated with recycling benzene. Moreover, this change can decrease the formation of by-products such as n-propylbenzene.

This change to the flow scheme of FIG. 2 consists of diverting some or all of the recycle benzene that flows through the line 146 to line 166. Of course, diverting all of the recycle flow from line 146 to line 166 would in effect eliminate line 146 from the flow scheme in FIG. 2. According to this changed flow scheme, the diverted benzene flows through lines 166 and 142 and enters the transalkylation reactor 140, thereby increasing the phenyl/propyl ratio in the transalkylation reactor 140. The transalkylation effluent flows through the line 144, combines with undiverted recycle benzene, if any, flowing through the line 146, and passes to the alkylation reactors 110 and 120 as described previously. Because any phenyl groups diverted from line 146 to line 166 ultimately pass to the alkylation reactors 110 and 120, albeit via the transalkylation reactor 140, the phenyl/propyl ratio in the alkylation reactors 110 and 120 are unchanged. Thus, this change to the flow scheme in FIG. 2 increases the phenyl/propyl ratio in the transalkylation reactor 140 without decreasing the phenyl/propyl ratio in the alkylation reactors 110 and 120.

As mentioned previously, one result of this increased phenyl/propyl ratio in transalkylation at a constant phenyl/propyl ratio in alkylation can be to decrease alkylation catalyst deactivation caused by any TIPB. As the phenyl/propyl ratio in transalkylation increases, the conversion of DIPB and TIPB in transalkylation increases. As more moles of DIPB and TIPB are converted in transalkylation, fewer moles of unconverted DIPB and TIPB are present in the transalkylation effluent, and so fewer moles of DIPB and TIPB will be present in the alkylation feed. This should decrease the concentration of TIPB in alkylation and decrease the alkylation catalyst deactivation rate.

As mentioned previously, another result of this increased phenyl/propyl ratio in transalkylation at a constant phenyl/propyl ratio in alkylation can be to further reduce the capital and operating costs associated with recycling benzene. As the phenyl/propyl ratio in transalkylation increases, the conversion of DIPB and other polyisopropylbenzenes in transalkylation increases. As more moles of DIPB are converted in transalkylation, fewer moles of unconverted DIPB are present in the transalkylation effluent, and so fewer moles of DIPB need to be recirculated to transalkylation. Assuming as before a constant phenyl/propyl ratio in transalkylation, the costs associated with recycling benzene are decreased. As also mentioned previously, yet another result of this increase in phenyl/propyl ratio in transalkylation at the same phenyl/propyl ratio in alkylation can be less formation of n-propyl benzene. As the phenyl/propyl ratio in transalkylation increases at constant DIPB conversion, the transalkylation conditions become less severe, and consequently, the formation in transalkylation of n-propyl benzene, as well as other by-products, decreases.

The extents to which diverting to the transalkylation zone some or all of the recycle benzene causes these beneficial effects depends on the phenyl/alkyl is ratio in the transalkylation reaction zone prior to the diversion. In general, these benefits increase as the transalkylation phenyl/alkyl ratio decreases. Thus, if the transalkylation phenyl/alkyl ratio is low without diverting any of the benzene, such as a phenyl/alkyl ratio of about 3:1 or less in the case of cumene production, then the diversion of additional benzene is expected to produce the aforementioned beneficial results to a more significant extent.

TABLE 1

|  | EXAMPLE I | EXAMPLE II |
|---|---|---|
| Transalkylation Conditions |  |  |
| Rx 140 Avg. Temp., deg F. | 284 | 281 |
| Rx 140 Press., psig | 483 | 577 |
| DIPB LHSV, hr-1 | 0.661 | 0.665 |
| Overall LHSV, hr-1 | 2.03 | 2.01 |
| Phenyl/propyl, mol/mol | 2.52 | 2.48 |
| Transalkylation Results |  |  |
| DIPB conversion, % | 35.2 | 32.0 |
| Delta nPB/Delta cumene, wppm/wt. frac. | 394 | 388 |
| Alkylation Conditions |  |  |
| Rx 110 Inlet Temp., deg F. | 288 | 288 |
| Rx 110 Maximum Temp., deg F. | 311 | 311 |
| Rx 120 Inlet Temp., deg F. | 287 | 286 |
| Rx 120 Maximum Temp., deg F. | 308 | 307 |
| Rx 110 & 120 Avg. Press., psig | 495 | 495 |
| Propylene LHSV, hr-1 | 0.495 | 0.494 |
| Benzene/Propylene, mol/mol | 3.01 | — |
| Phenyl/propyl, mol/mol | 3.01 | 2.86 |
| Effluent/feed recycle, wt/wt | 4.03 | 3.78 |
| Alkylation Results |  |  |
| Propylene conversion, % | 100 | 100 |
| DIPB produced in alkylation, mass units | 291 | 213 |
| Delta nPB/Delta cumene, wppm/wt. frac. | 188 | 201 |
| Overall Results |  |  |
| Cumene product yield, wt-% | 99.4–99.5 | 98.7–99.3 |
| Cumene product purity, wt-% | 99.98 | 99.97 |
| nPB in cumene product, wppm | 234 | 237 |

EXAMPLE III

Example III describes the benefits achieved by embodiments of the present invention that introduce into alkylation beds other than the first alkylation bed of a multibed alkylation reaction zone portions of transalkylation effluent in cooperation with additional quantities of alkylation substrate. In contrast to the previous description of FIG. 1, which was directed to a process that produces cumene, Example III illustrates a process that produces ethylbenzene by alkylating benzene with ethylene using a variation of the flow scheme of FIG. 1. Nevertheless, it is believed that the benefits illustrated by Example III have corresponding benefits in a cumene process, namely a decrease in the formation of diphenylpropane and alkylated diphenylpropanes.

Figure 3:
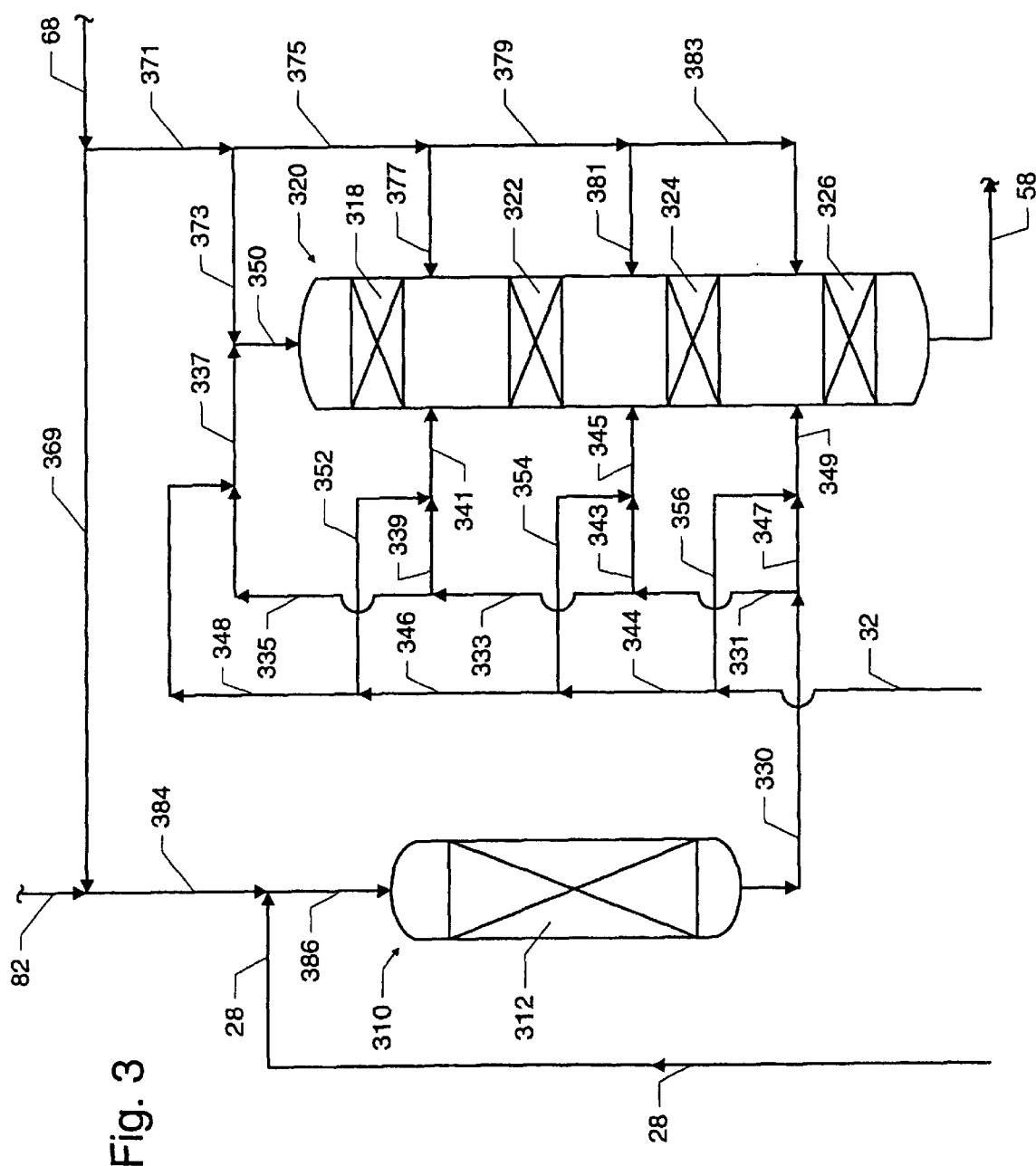

Example III is based on laboratory experiments, pilot plant testing, engineering calculations, and actual operating experience with similar processes. In describing Example II, reference is made to FIG. 3, which shows the flow scheme for Example III and illustrates an embodiment of this invention. FIG. 3 shows a variation of the process shown in FIG. 1, and therefore for the sake of brevity lines and equipment that are shown in FIG. 1 are not again shown in FIG. 3. Lines in FIG. 3 which interconnect with lines in FIG. 1 have the same line numbers in both FIGS. 1 and 3. However, references to lines and equipment shown in FIG. 1 will be made in the context of their use in an ethylbenzene process.

Referring now to FIG. 3, fresh benzene flows through line 28 and mixes with a stream in line 384 that contains recycle benzene provided via lines 68 and 369 and also contains recycle diethylbenzenes and recycle triethylbenzenes provided via line 82. The mixture flows through line 386 and enters a transalkylation reaction vessel 310 containing a bed 312 of transalkylation catalyst comprising zeolite Y operated at transalkylation conditions including a transalkylation temperature and a transalkylation liquid hourly space velocity (LHSV). The transalkylation effluent flows from vessel 310 via line 330. In this Example III, the transalkylation temperature is 193° C. (379° F.), or 31° C. (56° F.) below the outlet temperature of each of the four alkylation beds in alkylation reaction vessel 320. For some combinations of transalkylation catalysts and transalkylation liquid hourly space velocities, the transalkylation temperature may be above the desired inlet temperature of the alkylation beds, in which case the transalkylation effluent in line 330 would be cooled to the desired alkylation bed inlet temperature. After cooling, if any, transalkylation effluent in line 330 is divided into at least two portions via lines 347, 349, 331, 343, 345, 333, 339, 341, 335, 337, and 350, which supply a portion of the transalkylation effluent for each of the four alkylation beds in vessel 320. Vessel 320 contains a series of four alkylation beds 318, 322, 324, and 326, which all contain alkylation catalyst comprising zeolite beta operated at alkylation conditions including an alkylation outlet temperature, which in this Example III is 224° C. (435° F.). The portion of the transalkylation effluent for bed 318 flows through lines 331, 333, 335, 337, and 350 and enters vessel 320 upstream of bed 318. Similarly, the portion of transalkylation effluent for bed 322 flows through lines 331, 333, 339 and 341; the portion of transalkylation effluent for bed 324 flows through lines 331, 343, and 345; and the portion of transalkylation effluent for bed 326 flows through lines 347 and 349. Line 32 supplies ethylene for the alkylation beds in vessel 320. Ethylene for bed 318 flows through lines 344, 346, 348, 337, and 350; ethylene for bed 322 flows through lines 344, 346, 352, and 341; ethylene for bed 324 flows through lines 344, 354, and 345; and ethylene for bed 326 flows through lines 356 and 349. Line 68 delivers recycle benzene for the transalkylation bed 312 to line 369 and supplies recycle benzene for the alkylation beds in vessel 320 via line 371. Benzene for alkylation bed 318 flows through lines 373 and 350 and enters upstream of bed 318; benzene for bed 322 flows through lines 375 and 377; benzene for bed 324 flows through lines 375, 379, and 381; and benzene for bed 326 flows through lines 375, 379, and 383.

Alkylation effluent from alkylation bed 326 flows from vessel 320 via line 58. To avoid repetition, the separation of the alkylation effluent in this Example III can be described briefly with reference to FIG. 1. Thus, column 40 functions as a benzene column, column 60 functions as a deethanizer, column 70 functions as an ethylbenzene column, and column 80 functions as a heavies column. These four columns produce streams including an overhead stream comprising ethane and water in line 66, a recycle stream comprising benzene in line 68, an overhead stream comprising ethylbenzene product in line 72, a recycle stream comprising diethylbenzenes and triethylbenzenes in line 82, and a heavy aromatics stream comprising diphenylethane (DPE) and alkylated diphenylethanes (DPEs) in line 76.

Example III illustrates four cases, each of which has a different distribution to the four alkylation beds of portions of the transalkylation effluent and/or of recycle benzene for alkylation, which are also used for quench. In all four cases, the flows of polyethylbenzenes, fresh benzene, and recycle benzene to transalkylation bed 312 are held constant, as is bed 312's outlet temperature of 193° C. (379° F.). In addition, in all four cases, the outlet temperatures of the four alkylation beds 318, 322, 324, and 326 are the same at 224° C. (435° F.), ethylene flow to each of the four alkylation beds is uniform and the same, and the total recycle benzene flow to the four alkylation beds is constant. Also, the net flow of ethylbenzene product is held constant in all four cases.

The results of Cases 1 through 4 are shown in Table 2. Case 1 is a base case, in which transalkylation effluent is introduced only into the first alkylation bed 318 but not into the other alkylation beds 322, 324, and 326. Thus, in Case 1, the entire transalkylation effluent passes to bed 318, with no portions of the transalkylation effluent passing directly to bed 322, 324, or 326. In this respect, Case 1 of this Example III corresponds to Example II, wherein the entire transalkylation effluent in line 144 passes via lines 148, 154, and 156 to the first alkylation reactor 110. Also, in Case 1, one-half of the recycle benzene for alkylation in line 371 passes directly to bed 318, and the other half passes directly to bed 322.

Cases 2, 3, and 4 show that passing portions of the transalkylation effluent into multiple alkylation beds decreases the net formation in alkylation of DPE and alkylated DPEs. With the distribution of recycle benzene for alkylation to the alkylation beds the same as in Case 1, the distribution of transalkylation effluent to alkylation beds 318, 322, 324, and 326 is 0%/40%/30%/30% respectively (i.e., these portions are used) for Case 2 and 50%/10%/10%/30% respectively (i.e., these portions are used) for Case 3. Cases 2 and 3 show about a 2.4–2.5% decrease in the formation in alkylation zone 320 of DPE and alkylated DPEs relative to Case 1. Case 4 shows a further synergistic effect that decreases the formation of DPE and alkylated DPEs when the distribution of recycle benzene for alkylation zone 320 between beds 318 and 322 is skewed towards bed 318. Thus, with the same distribution of transalkylation effluent to the alkylation beds as in Case 2, for Case 4 three-quarters of the recycle benzene in line 371 passes to bed 318 and only one-quarter passes directly to bed 322. Accordingly, in Case 4, the formation in alkylation of DPE and alkylated DPEs decreases even more significantly, to only 83.5% of that which forms in Case 1. If all of the recycle benzene in line 371 is passed to bed 318, there would be a still further decrease in the formation in alkylation zone 320 of DPE and alkylated DPEs. Thus, passing portions of the transalkylation effluent into a plurality of alkylation beds is more advantageous than passing the entire transalkylation effluent into only the first bed of a series of alkylation beds.

TABLE 2

| PARAMETER | BED | CASE 1 | CASE 2 | CASE 3 | CASE 4 |
| --- | --- | --- | --- | --- | --- |
| Distribution of Transalkylation Effluent | 318 | 100 | 0 | 50 | 0 |
|  | 322 | 0 | 40 | 10 | 40 |
| to Alkylation Beds, % of Total Transalkylation effluent to Alkylation Beds | 324 | 0 | 30 | 10 | 30 |
|  | 326 | 0 | 30 | 30 | 30 |
| Distribution of Benzene to Alkylation Beds, % of Total Benzene to Alkylation Beds | 318 | 50 | 50 | 50 | 75 |
|  | 322 | 50 | 50 | 50 | 25 |
|  | 324 | 0 | 0 | 0 | 0 |
|  | 326 | 0 | 0 | 0 | 0 |
| Phenyl/Ethyl Molar Ratio in Alkylation Beds, mol/mol | 318 | Base | 1.08* Base | 1.02* Base | 1.62* Base |
|  | 322 | Base | 1.02* Base | 1.01* Base | 1.03* Base |
|  | 324 | Base | 0.98* Base | 0.98* Base | 0.98* Base |
|  | 326 | Base | 1.00* Base | 1.00* Base | 1.00* Base |
| Total Net Formation of DPE and Alkylated DPEs in Alkylation Beds, mass/time |  | Base | 0.976* Base | 0.975* Base | 0.835* Base |

What is claimed is:

1. A process for producing isopropyl aromatic hydrocarbons, said process comprising:

a) passing a first transalkylation feed stream comprising an aromatic substrate hydrocarbon to a transalkylation reaction zone, passing a second transalkylation feed stream comprising a first isopropyl aromatic hydrocarbon having more than one isopropyl group to said transalkylation reaction zone, transalkylating said aromatic substrate hydrocarbon with said first isopropyl aromatic hydrocarbon in the presence of a first solid catalyst in said transalkylation reaction zone to produce a second isopropyl aromatic hydrocarbon having at least one more isopropyl group than said aromatic substrate hydrocarbon, and recovering from said transalkylation reaction zone a transalkylation effluent stream comprising said aromatic substrate hydrocarbon and said second isopropyl aromatic hydrocarbon;

b) passing a first alkylation feed stream comprising propylene to a first bed of an alkylation reaction zone, passing a first aliquot portion of said transalkylation effluent stream to said first bed, and alkylating said aromatic substrate hydrocarbon with propylene in the presence of a second solid catalyst in said first bed to produce a first bed effluent stream comprising said second isopropyl aromatic hydrocarbon;

c) passing at least a portion of said first bed effluent stream and a second aliquot portion of said transalkylation effluent stream to a second bed of said alkylation reaction zone, alkylating said aromatic substrate hydrocarbon with propylene in the presence of a third solid catalyst in said second bed to produce said second isopropyl aromatic hydrocarbon; and d) recovering said second isopropyl aromatic hydrocarbon from said process.

2. The process of claim 1 wherein said at least a portion of said first bed effluent stream comprises an aliquot portion of said first bed effluent stream.

3. The process of claim 1 further characterized in that said passing of said at least a portion of said first bed effluent stream to said second bed comprises the steps of:

a) passing said at least a portion of said first bed effluent stream to a third bed, alkylating said aromatic substrate hydrocarbon with propylene in the presence of a fourth solid catalyst in said third bed and withdrawing a third bed effluent stream comprising said second isopropyl aromatic hydrocarbon from said third bed; and b) passing at least a portion of said third bed effluent stream to said second bed.

4. The process of claim 3 further characterized in that a third aliquot portion of said transalkylation effluent stream is passed to said third bed.

5. The process of claim 1 further characterized in that a second alkylation feed stream comprising propylene is passed to said second bed of said alkylation reaction zone.

6. The process of claim 1 wherein said first bed effluent stream comprises propylene.

7. The process of claim 1 further characterized in that said process comprises the steps of:

e) withdrawing from said second bed a second bed effluent stream comprising said second isopropyl aromatic hydrocarbon and said first isopropyl aromatic hydrocarbon;

f) separating said second bed effluent stream into a product stream comprising said second isopropyl aromatic hydrocarbon and a recycle stream comprising said first isopropyl aromatic hydrocarbon; and g) forming at least a portion of said second transalkylation feed stream from at least a portion of said recycle stream.

8. The process of claim 1 further characterized in that said process comprises the steps of:

e) withdrawing from said second bed a second bed effluent stream comprising said second isopropyl aromatic hydrocarbon and said aromatic substrate hydrocarbon;

f) separating said second effluent stream into a product stream comprising said second isopropyl aromatic hydrocarbon and a recycle stream comprising said aromatic substrate hydrocarbon; and g) forming at least a portion of said first transalkylation feed stream from at least a portion of said recycle stream.

9. The process of claim 8 wherein said forming at least a portion of said first transalkylation feed stream from at least a portion of said recycle stream comprises forming at least a portion of said first transalkylation feed stream from a first portion of said recycle stream and further characterized in that a second portion of said recycle stream is passed to said first bed.

10. The process of claim 8 wherein said forming at least a portion of said first transalkylation feed stream from at least a portion of said recycle stream comprises forming at least a portion of said first transalkylation feed stream from a first portion of said recycle stream and further characterized in that a second portion of said recycle stream is passed to said second bed.

11. The process of claim 1 wherein said first solid catalyst comprises a zeolite selected from the group consisting of zeolite Y, zeolite beta, ZSM-5, PSH-3, MCM-22, MCM-36, MCM49, and MCM-56.

12. The process of claim 1 wherein said second solid catalyst comprises a zeolite selected from the group consisting of zeolite Y, zeolite beta, ZSM-5, PSH-3, MCM-22, MCM-36, MCM49, and MCM-56.

13. The process of claim 1 wherein said third solid catalyst comprises a zeolite selected from the group consisting of zeolite Y, zeolite beta, ZSM-5, PSH-3, MCM-22, MCM-36, MCM49, and MCM-56.

14. The process of claim 1 wherein said first solid catalyst comprises zeolite Y, said second solid catalyst comprises zeolite beta, and said third solid catalyst comprises zeolite beta.

15. The process of claim 1 wherein said aromatic substrate hydrocarbon comprises benzene, and said second isopropyl aromatic hydrocarbon comprises cumene.

16. The process of claim 1 wherein said transalkylation effluent stream comprises an aromatic selected from the group consisting of a triisopropyl aromatic, a tetraisopropyl aromatic, a pentaisopropyl aromatic, a hexaisopropyl aromatic, and a diphenylpropane.

17. The process of claim 1 further characterized in that at least one of said first bed and said second bed operates under at least partial liquid phase conditions.

18. The process of claim 1 further characterized in that said alkylating occurs at a temperature of 250 to 350° F.

19. The process of claim 1 further characterized in that said alkylating occurs at a molar ratio of phenyl groups per isopropyl group of less than 3:1.

20. The process of claim 1 wherein said first solid catalyst, said second solid catalyst, and said third solid catalyst have the same composition.

21. The process of claim 1 wherein said transalkylation reaction zone and said alkylation reaction zone are contained in a common vessel.

22. The process of claim 1 further characterized in that a second alkylation feed stream comprising propylene and a third alkylation feed stream comprising said aromatic substrate hydrocarbon are passed to a third bed of said alkylation reaction zone, said aromatic substrate hydrocarbon is alkylated with propylene in the presence of a fourth solid catalyst in said third bed to produce a third bed effluent stream, and at least a portion of said third bed effluent stream is passed to said first bed.

23. The process of claim 1 wherein said passing of said at least a portion of said first bed effluent stream to said second bed comprises passing a first aliquot portion of said first bed effluent stream to said second bed and further characterized in that a second aliquot portion of said first bed effluent stream is recycled to said first bed.

24. The process of claim 23 further characterized in that said first bed operates at a temperature of from 250 to 350° F.

25. The process of claim 1 further characterized in that a second bed effluent stream comprising said second isopropyl aromatic hydrocarbon is withdrawn from said second bed, and an aliquot portion of said second bed effluent stream is recycled to said first bed.

26. The process of claim 1 further characterized in that a second bed effluent stream comprising said second isopropyl aromatic hydrocarbon is withdrawn from said second bed, and an aliquot portion of said second bed effluent stream is recycled to said second bed.

27. A process for producing isopropyl aromatic hydrocarbons, said process comprising:

a) passing a first transalkylation feed stream comprising an aromatic substrate hydrocarbon to a transalkylation reaction zone, passing a second transalkylation feed stream comprising a first isopropyl aromatic hydrocarbon having more than one isopropyl group to said transalkylation reaction zone, transalkylating said aromatic substrate hydrocarbon with said first isopropyl aromatic hydrocarbon in the presence of a first solid catalyst in said transalkylation reaction zone to produce a second isopropyl aromatic hydrocarbon having at least one more isopropyl group than said aromatic substrate hydrocarbon, and recovering from said transalkylation reaction zone a transalkylation effluent stream comprising said aromatic substrate hydrocarbon and said second isopropyl aromatic hydrocarbon;

b) passing a first alkylation feed stream comprising propylene to a first bed of an alkylation reaction zone, passing a first aliquot portion of said transalkylation effluent stream to said first bed, and alkylating said aromatic substrate hydrocarbon with propylene in the presence of a second solid catalyst in said first bed to produce a first bed effluent stream comprising said aromatic substrate hydrocarbon and said second isopropyl aromatic hydrocarbon;

c) passing a second alkylation feed stream comprising propylene to a second bed of said alkylation reaction zone, passing at least a portion of said first bed effluent stream to said second bed, and alkylating said aromatic substrate hydrocarbon with propylene in the presence of a third solid catalyst in said second bed to produce a second bed effluent stream comprising said aromatic substrate hydrocarbon and said second isopropyl aromatic hydrocarbon;

d) passing a third alkylation feed stream comprising propylene to a third bed of said alkylation reaction zone, passing at least a portion of said second bed effluent stream to said third bed, passing a second aliquot portion of said transalkylation effluent stream to said third bed, and alkylating said aromatic substrate hydrocarbon with propylene in the presence of a fourth solid catalyst in said third bed to produce a third bed effluent stream comprising said aromatic substrate hydrocarbon and said second isopropyl aromatic hydrocarbon;

e) passing a fourth alkylation feed stream comprising propylene to a fourth bed of said alkylation reaction zone, passing at least a portion of said third bed effluent stream to said fourth bed, alkylating said aromatic substrate hydrocarbon with propylene in the presence of a fifth solid catalyst in said fourth bed to produce a fourth bed effluent stream comprising said aromatic substrate hydrocarbon and said second isopropyl aromatic hydrocarbon;

f) recovering said second isopropyl aromatic hydrocarbon from said process.

28. The process of claim 27 wherein said passing of said at least a portion of said second bed effluent stream to said third bed comprises passing a first aliquot portion of said second bed effluent stream to said third bed and further characterized in that a second aliquot portion of said second bed effluent stream is recycled to said first bed.

29. The process of claim 27 further characterized in that a fourth bed effluent stream comprising said second isopropyl aromatic hydrocarbon is withdrawn from said fourth bed, and an aliquot portion of said fourth bed effluent stream is recycled to said first bed.

30. The process of claim 27 further characterized in that a fourth bed effluent stream comprising said second isopropyl aromatic hydrocarbon is withdrawn from said fourth bed, and an aliquot portion of said fourth bed effluent stream is recycled to said third bed.

31. A process for producing isopropyl aromatic hydrocarbons, said process comprising:

a) passing a first transalkylation feed stream comprising an aromatic substrate hydrocarbon to a transalkylation reaction zone, passing a second transalkylation feed stream comprising a first isopropyl aromatic hydrocarbon having more than one isopropyl group to said transalkylation reaction zone, transalkylating said aromatic substrate hydrocarbon with said first isopropyl aromatic hydrocarbon in the presence of a first solid catalyst in said transalkylation reaction zone to produce a second isopropyl aromatic hydrocarbon having at least one more isopropyl group than said aromatic substrate hydrocarbon, and recovering from said transalkylation reaction zone a transalkylation effluent stream comprising said aromatic substrate hydrocarbon and said second isopropyl aromatic hydrocarbon;

b) passing a first alkylation feed stream comprising propylene to a first bed of an alkylation reaction zone, passing a first aliquot portion of said transalkylation effluent stream to said first bed, and alkylating said aromatic substrate hydrocarbon with propylene in the presence of a second solid catalyst in said first bed to produce a first bed effluent stream comprising said aromatic substrate hydrocarbon and said second isopropyl aromatic hydrocarbon;

c) passing a second alkylation feed stream comprising propylene to a second bed of said alkylation reaction zone, passing at least a portion of said first bed effluent stream to said second bed, alkylating said aromatic substrate hydrocarbon with propylene in the presence of a third solid catalyst in said second bed, and withdrawing a second bed effluent stream comprising said second isopropyl aromatic hydrocarbon from said second bed; and d) passing a third alkylation feed stream comprising propylene to a third bed of said alkylation reaction zone, passing at least a portion of said second bed effluent stream to said third bed, passing a second aliquot portion of said transalkylation effluent stream to said third bed, and alkylating said aromatic substrate hydrocarbon with propylene in the presence of a fourth solid catalyst in said third bed to produce said second isopropyl aromatic hydrocarbon; and e) recovering said second isopropyl aromatic hydrocarbon from said process.

32. A process for the production of cumene, said process comprising:

a) contacting an aromatic feed comprising benzene, a benzene recycle stream comprising benzene, and a diisopropylbenzene stream comprising diisopropylbenzene in a transalkylation reaction zone with a transalkylation catalyst at transalkylation conditions to produce a transalkylation zone effluent comprising benzene, cumene, and diisopropylbenzene;

b) contacting a first aliquot portion of said transalkylation zone effluent and a first olefin feed comprising propylene and propane in a first bed of an alkylation reaction zone with a first solid alkylation catalyst at alkylation conditions to provide a first alkylation bed effluent comprising propane, benzene, cumene, diisopropylbenzene, and a heavies hydrocarbon;

c) contacting a second aliquot portion of said transalkylation zone effluent and a second olefin feed comprising propylene and propane in a second bed of said alkylation reaction zone with a second solid alkylation catalyst at alkylation conditions to provide a second alkylation bed effluent comprising propane, benzene, cumene, diisopropylbenzene, and said heavies hydrocarbon;

d) separating said second alkylation bed effluent in a benzene separation zone into a benzene fraction comprising benzene and propane and a benzene bottoms stream comprising cumene, diisopropylbenzene, and said heavies hydrocarbon;

e) separating said benzene fraction in a light ends column into said benzene recycle stream and a light ends stream comprising propane;

f) separating said benzene bottoms stream into a product stream comprising cumene and a cumene bottoms stream comprising diisopropylbenzene and said heavies hydrocarbon; and g) separating said cumene bottoms stream into a heavies stream comprising said heavies hydrocarbon that is removed from the process and said diisopropylbenzene stream.

33. The process of claim 32 further characterized in that water is passed to said alkylation reaction zone and said light ends stream comprises water.

* * * * *